United States Patent
Hyde et al.

(10) Patent No.: US 10,254,565 B2
(45) Date of Patent: Apr. 9, 2019

(54) OPHTHALMIC DEVICES AND RELATED METHODS

(71) Applicant: Elwha LLC, Bellevue, WA (US)

(72) Inventors: Roderick A. Hyde, Redmond, WA (US); Melanie K. Kitzan, Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 33 days.

(21) Appl. No.: 15/221,362

(22) Filed: Jul. 27, 2016

(65) Prior Publication Data

US 2018/0031865 A1    Feb. 1, 2018

(51) Int. Cl.
| | | |
|---|---|---|
| *G02C 7/08* | (2006.01) | |
| *A61F 2/16* | (2006.01) | |
| *A61B 5/0488* | (2006.01) | |
| *A61B 3/11* | (2006.01) | |
| *A61B 3/113* | (2006.01) | |

(Continued)

(52) U.S. Cl.
CPC .............. *G02C 7/083* (2013.01); *A61B 3/112* (2013.01); *A61B 3/113* (2013.01); *A61B 5/0492* (2013.01); *A61B 5/04888* (2013.01); *A61B 5/05* (2013.01); *A61B 5/6821* (2013.01); *A61F 2/1627* (2013.01); *A61F 2/1635* (2013.01); *A61F 2/1656* (2013.01); *G02C 7/04* (2013.01); *A61B 2562/0219* (2013.01); *A61F 2250/0002* (2013.01); *G02C 2202/16* (2013.01); *G02C 2202/20* (2013.01)

(58) Field of Classification Search
CPC .......... G02C 7/083; G02C 7/04; A61F 2/1635; A61F 2/1656; A61B 3/112; A61B 3/113; A61B 5/05; A61B 5/6821
See application file for complete search history.

(56) References Cited

U.S. PATENT DOCUMENTS

| | | |
|---|---|---|
| 6,638,304 B2 | 10/2003 | Azar |
| 7,041,133 B1 | 5/2006 | Azar |

(Continued)

OTHER PUBLICATIONS

U.S. Appl. No. 14/807,756, filed Jul. 23, 2015, Cheatham et al.

(Continued)

*Primary Examiner* — David H Willse
*Assistant Examiner* — Tiffany Shipmon
(74) *Attorney, Agent, or Firm* — Dorsey & Whitney LLP

(57) ABSTRACT

Embodiments disclosed herein are related to systems including at least one ophthalmic device (e.g., at least one intraocular lens or at least one contact lens) and methods of using the at least one ophthalmic device. The ophthalmic device includes a switchable lens that can selectively change a focal length thereof. The ophthalmic device also includes a plurality of sensors disposed therein or thereon that sense one or more characteristics. At least one of the plurality of sensors can sense one or more electromyography signals associated with a ciliary muscle of the eye. At least another of the plurality of sensors can sense one or more accelerations of the eye, one or more electromagnetic signals, one or more magnetic fields, one or more additional electromyography signals, or another suitable characteristic. The systems can also include at least one controller configured to direct changing the focal length of the switchable lens responsive to the characteristics sensed by the sensors.

40 Claims, 15 Drawing Sheets

(51) Int. Cl.
*A61B 5/0492* (2006.01)
*A61B 5/05* (2006.01)
*A61B 5/00* (2006.01)
*G02C 7/04* (2006.01)

(56) References Cited

U.S. PATENT DOCUMENTS

| | | | |
|---|---|---|---|
| 8,043,370 | B2 | 10/2011 | Bretthauer et al. |
| 8,216,309 | B2 | 7/2012 | Azar |
| 8,992,610 | B2 | 3/2015 | Blum et al. |
| 9,063,351 | B1 * | 6/2015 | Ho ............ G02C 7/04 |
| 9,254,189 | B2 | 2/2016 | Azar |
| 9,268,155 | B2 | 2/2016 | Pugh et al. |
| 2003/0018383 | A1 | 1/2003 | Azar |
| 2003/0210377 | A1 * | 11/2003 | Blum ............ G02B 27/017 |
| | | | 351/159.4 |
| 2006/0206205 | A1 | 9/2006 | Azar |
| 2007/0260307 | A1 | 11/2007 | Azar |
| 2008/0177170 | A1 * | 7/2008 | Roberts ............ A61B 3/113 |
| | | | 600/409 |
| 2009/0105817 | A1 | 4/2009 | Bretthauer et al. |
| 2009/0326652 | A1 | 12/2009 | Azar |
| 2012/0162600 | A1 | 6/2012 | Pugh et al. |
| 2012/0239144 | A1 | 9/2012 | Azar |
| 2013/0073038 | A1 * | 3/2013 | Azar ............ A61F 2/147 |
| | | | 623/6.22 |
| 2014/0002789 | A1 | 1/2014 | Pugh et al. |
| 2014/0156000 | A1 * | 6/2014 | Campin ............ A61B 5/0488 |
| | | | 623/6.37 |
| 2014/0240656 | A1 * | 8/2014 | Pugh ............ G02C 7/04 |
| | | | 351/159.03 |
| 2015/0057748 | A1 | 2/2015 | Azar |

OTHER PUBLICATIONS

U.S. Appl. No. 14/807,719, filed Jul. 23, 2015, Hyde et al.
U.S. Appl. No. 14/807,673, filed Jul. 23, 2015, Hyde et al.
Palumbo et al., "Charge Pump Circuits: An Overview on Design Strategies and Topologies"; IEEE Circuits and Systems Magazine; First Quarter 2010, pp. 31-45.
Plyarinos, et al. "Charge Pumps: An Overview", Department of Electrical and Computer Engineering, University of Toronto, 2003, pp. 1-7.
Findl, MD, "Intraocular Lens Materials and Design" Achieving Excellence in Cataract Surgery, Chaper 12, 2009, pp. 95-108.
Tripti, et al., "Materials for intraocular lenses (IOLs): Review of developments to achieve biocompatibility" e-Polymers 2009, No. 124, ISSN 1618-7229, published: Oct. 27, 2009; pp. 1-23.
Tetz et al., "New Hydrophobic IOL Materials and Understanding the Science of Glistenings"; Current Eye Research, ISSN: 0271-3683 print / 1460-2202 online, Published online: Jan. 26, 2015. pp. 969-981.
Argal, "Newer intraocular lens materials and design" Journal of Clinical Ophthalmology and Research—May-Aug. 2013—vol. 1—Issue 2, pp. 113-117.

* cited by examiner

OPHTHALMIC DEVICES AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Focal correction can improve vision of an individual. For example, glasses, contact lenses, and intraocular lenses (IOLs), such as pseudophakic IOLs, aphikic IOLs, or phakic IOLs (PIOLS), can be used to correct the vision of an individual.

Typical IOLs can include monofocal, multifocal, or accommodative configurations. IOLs can include an optic element (e.g., lens) and haptic elements (e.g., arms or wings configured to aid in positioning the IOL). Such configurations can be limited to focusing either on near or far vision without selectively modifiable adjustment therebetween.

SUMMARY

Embodiments disclosed herein are related to systems including at least one ophthalmic device (e.g., at least one intraocular lens or at least one contact lens) and methods of using the at least one ophthalmic device. The at least one ophthalmic device includes at least one switchable lens that can selectively change a focal length thereof. The at least one ophthalmic device also includes a plurality of sensors that sense one or more characteristics. At least one of the plurality of sensors can sense one or more electromyography (EMG) signals associated with a ciliary muscle of an eye of an individual. At least another of the plurality of sensors can sense one or more accelerations of the eye, one or more EMG signals, one or more magnetic fields, one or more additional EMG signals, or another suitable characteristic. The systems can also include at least one controller configured to direct the at least one switchable lens to change the focal length thereof responsive to the one or more characteristics sensed by the plurality of sensors.

In an embodiment, a system is disclosed. The system includes at least one ophthalmic device having at least one switchable lens configured to selectively switch a focal length thereof. The at least one ophthalmic device also includes at least one first sensor configured to sense one or more EMG signals. The at least one first sensor includes at least two electrodes. At least one of the at least two electrodes is disposed in a portion of the at least one ophthalmic device that is at least proximate to a ciliary muscle of an eye of an individual when the at least one ophthalmic device is placed in or on the eye. The at least one first sensor is configured to transmit one or more first sensing signals responsive to sensing one or more EMG signals. The at least one ophthalmic device further includes at least one second sensor that is distinct from the at least one first sensor. The at least one second sensor is configured to transmit one or more second sensing signals responsive to sensing one or more characteristics. The system also includes at least one controller communicably coupled to the at least one switchable lens, the at least one first sensor, and the at least one second sensor. The at least one controller is configured to direct the at least one switchable lens to selectively switch the focal length thereof responsive to the one or more first sensing signals and the one or more second sensing signals.

In an embodiment, a method of adjusting a focal length of at least one ophthalmic device is disclosed. The method includes sensing one or more EMG signals with at least one first sensor disposed in the at least one ophthalmic device and located at least proximate to a ciliary muscle of an eye of an individual that the at least one ophthalmic device is placed in or on. The method also includes transmitting one or more first sensing signals from the at least one first sensor to at least one controller responsive to sensing the one or more EMG signals. Additionally, the method includes sensing one or more characteristics with at least one second sensor disposed in the at least one ophthalmic device. The at least one second sensor is distinct from the at least one first sensor. The method further includes transmitting one or more second sensing signals from the at least one second sensor to the at least one controller responsive to sensing the one or more characteristics. The method additionally includes, with the at least one controller, comparing the one or more first sensing signals and the one or more second sensing signals to determine whether the ciliary muscle at least partially generated the one or more EMG signals sensed with the at least one first sensor. The method also includes, with the at least one controller, selectively modifying the focal length of at least one switchable lens of the at least one ophthalmic device responsive to the determining.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Embodiments disclosed herein are related to systems including at least one ophthalmic device (e.g., at least one intraocular lens or at least one contact lens) and methods of using the at least one ophthalmic device. The at least one ophthalmic device includes at least one switchable lens that can selectively change a focal length thereof. The at least one ophthalmic device also includes a plurality of sensors that sense one or more characteristics. At least one of the plurality of sensors can sense one or more EMG signals associated with a ciliary muscle of an eye of an individual. At least another of the plurality of sensors can sense one or more accelerations of the eye, one or more electromagnetic signals, one or more magnetic fields, one or more additional EMG signals, or another suitable characteristic. The systems can also include at least one controller configured to direct the at least one switchable lens to change the focal length thereof responsive to the one or more characteristics sensed by the plurality of sensors.

Figure 1A:
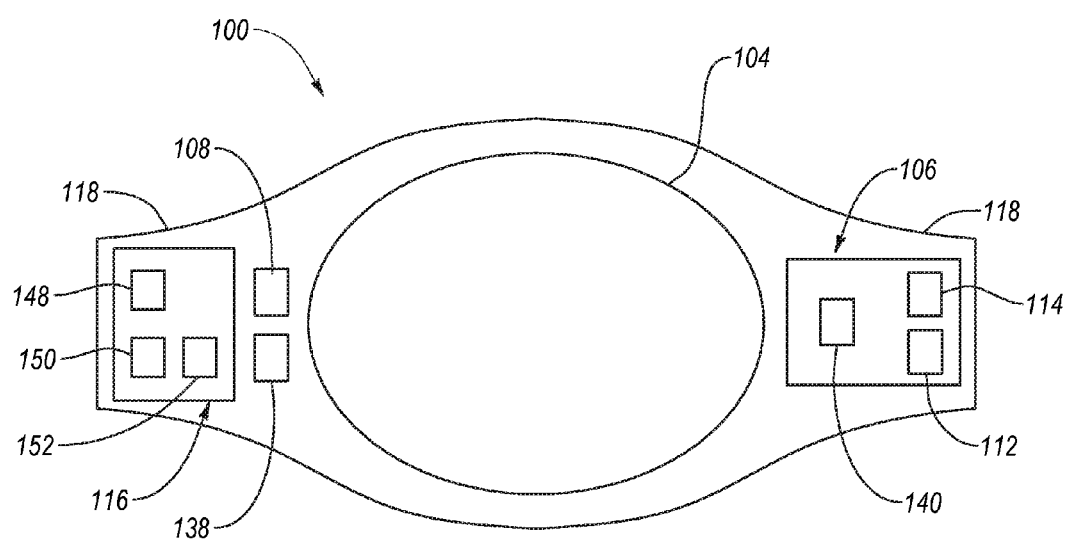
FIG. 1A is a schematic illustration of an ophthalmic device, according to an embodiment.
Figure 1B:
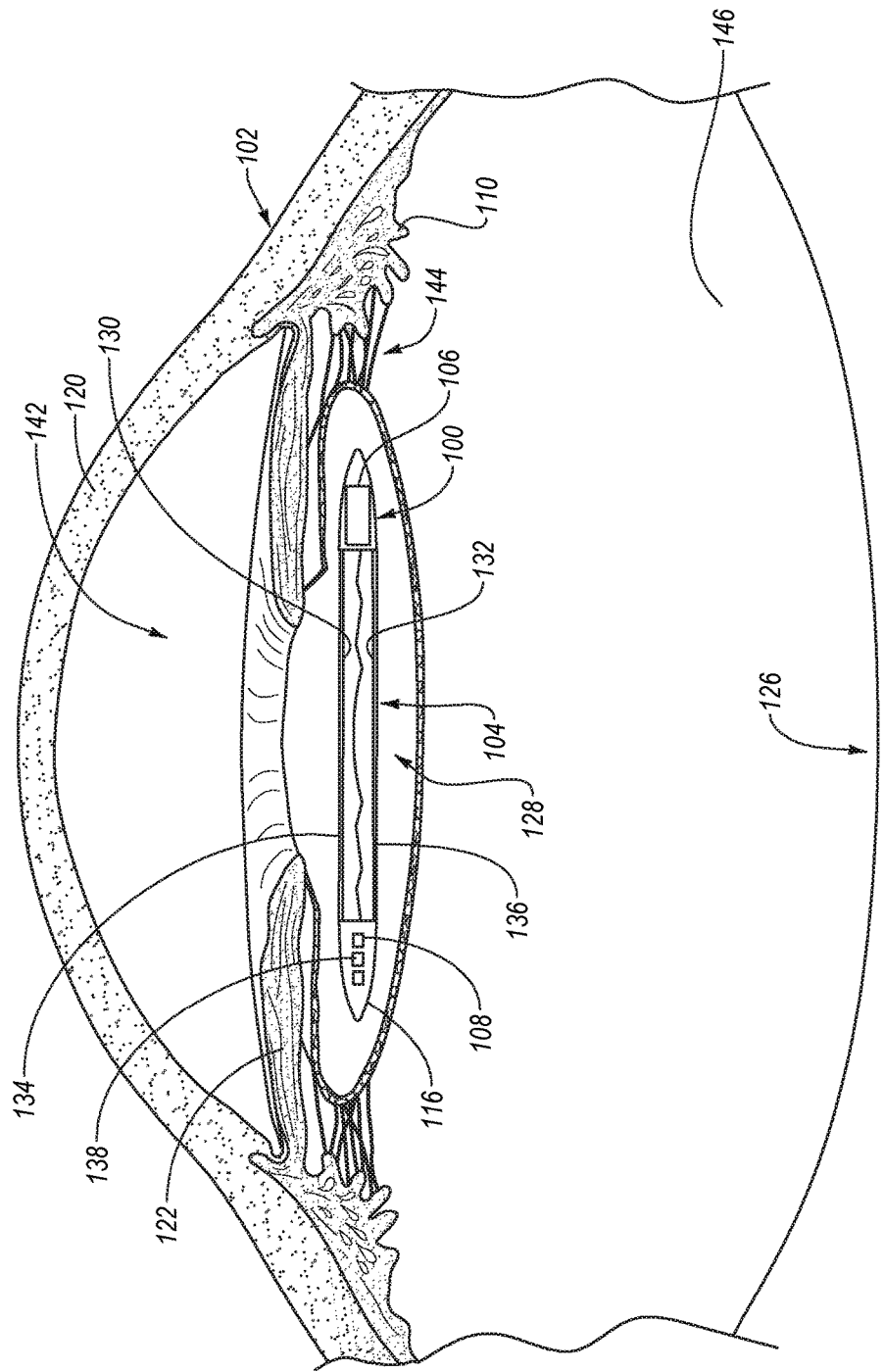
FIG. 1B is a side, cross-sectional view of the ophthalmic device of FIG. 1A implanted in an eye of an individual.

FIG. 1A is a schematic illustration of an ophthalmic device 100, according to an embodiment. FIG. 1B is a side, cross-sectional view of the ophthalmic device 100 implanted in an eye 102 of an individual. The ophthalmic device 100 includes at least one switchable lens 104 configured to selectively switch a focal length thereof. The ophthalmic device 100 also includes at least one first sensor 106 and at least one second sensor 108 distinct from the first sensor 106. The first sensor 106 is configured to sense one or more EMG signals from at least a ciliary muscle 110 (FIG. 1B) of an eye 102 (FIG. 1B). For example, the first sensor 106 can include at least two electrodes (e.g., first and second electrodes 112, 114). The second sensor 108 is configured to sense at least one of one or more characteristics, such as one or more accelerations associated with eye rotation, one or more electromagnetic signals, one or more changes in an identifiable magnetic field, or other suitable characteristic associated with the eye. The ophthalmic device 100 also includes at least one controller 116 that is communicably coupled to one or more components of the ophthalmic device 100. For example, the controller 116 can be communicably coupled to one or more of the at least one of the switchable lens 104, the first sensor 106, or the second sensor 108. The controller 116 is configured to direct the at least one switchable lens 104 to selectively switch the focal length thereof.

In the illustrated embodiment, the ophthalmic device 100 is an intraocular lens configured to be implanted into the eye 102 of the individual. For example, the ophthalmic device 100 can be configured to fit in or on one or more anatomical structures of the eye 102. The ophthalmic device 100 can include one or more haptics 118. The ophthalmic device 100 can be configured to focus light onto a surface of a retina 126 (FIG. 1B) of the individual. The ophthalmic device 100 can be configured to augment or correct visual deficiencies of the individual or to replace a natural lens of the individual, such as with cataract surgeries.

Referring specifically to FIG. 1A, the haptics 118 can be configured as wings extending away from the switchable lens 104. The haptics 118 can be coupled to the switchable lens 104 to form a multi-piece (e.g., c-loop, j-loop, or modified j-loop) or single piece ophthalmic device 100. In an embodiment, the haptics 118 can be configured as arms or struts having an elbow or bend. The arms can be similar to the wings shown in FIG. 1A, with one or more portions of a center of the wings removed therefrom. In an embodiment, the haptics 118 can be angulated, substantially planar, or offset relative to the switchable lens 104.

Each of the switchable lens 104 and the haptics 118 is at least partially formed from any suitable biocompatible material. For example, the switchable lens 104 or the haptics 118 can include polymethylmethacrylate, hydrophobic acrylic (e.g., a foldable hydrophobic acrylic), a hydrophilic acrylic (e.g., (hydroxyethyl)methacrylate), or a hydrophobic silicone (e.g., polydimethoxysilicone).

Referring again to FIG. 1B, the eye 102 includes a cornea 120, an iris 122, a ciliary muscle 110, a retina 126 therebehind, and a plurality of rectus muscles (not shown) attached to the eye 102. The ophthalmic device 100 can be implanted in the eye 102. In an embodiment, the ophthalmic device 100 can replace the natural lens of the eye 102. In an embodiment, the eye 102 can include both the ophthalmic device 100 and the natural lens (not shown). For example, the ophthalmic device 100 can be implanted over the natural lens of the eye 102, in front of (e.g., in the anterior chamber 142) the iris 122, behind the iris 122 (e.g., in the posterior chamber 144 or the vitreous body 146), or internal to the natural lens (e.g., in the capsular bag 128 of the natural lens). In an embodiment, the natural lens can be absent from the eye 102 (e.g., the ophthalmic device 100 can replace the natural lens and can be placed in the anterior chamber 142, the posterior chamber 144, or internal to the capsular bag 128 that used to contain the natural lens). In an embodiment, at least one of the haptics 118 can be positioned on the ciliary muscle 110. For example, the ophthalmic device 100 can be at least partially disposed within the posterior chamber 144 or the capsular bag 128 of the natural lens. The switchable lens 104 of the ophthalmic device 100 can be located laterally at or near a center of the eye 102, with the haptics 118 extending laterally therefrom.

The ophthalmic device 100 and, more particularly, the switchable lens 104 can be configured to exhibit a switchable/modifiable focal length. In an embodiment, the switchable lens 104 can include at least one electro-optical material having an electrically-modifiable index of refraction. For example, the electro-optical material can include lithium niobate, lithium tantalite, a liquid crystal, or another electro-optical material. In an embodiment, the switchable lens 104 can include a plurality of electro-optical materials, such as at least a first electro-optical material and a second electro-optical material. The first electro-optical material can be different from or similar to the second electro-optical material. In an embodiment, the switchable lens 104 can include a passive material (e.g., a substantially electro-optically inert material) having a substantially fixed index of refraction (e.g., glass, polymethylmethacrylate, silicone, hydrophobic acrylic, electro-optical inert hydrophilic materials, etc.).

The switchable lens 104 can include a first outer surface 130 and a second outer surface 132 opposite the first outer surface 130. To provide a sufficient bias to induce a modified index of refraction in the electro-optical material, the ophthalmic device 100 can include a first lens electrode 134 and a second lens electrode 136. The first lens electrode 134 can be disposed on the first outer surface 130 and the second lens electrode 136 can be disposed on the second outer surface 132. The first and second lens electrodes 134, 136 can be configured to deliver or maintain an electrical bias across the switchable lens 104 effective to modify the index of refraction of the electro-optical material. The first and second lens electrodes 134, 136 can apply the electrical bias responsive to direction from the controller 116. For example, the ophthalmic device 100 can include at least one power source 138 (FIG. 1A) disposed in or on the ophthalmic device 100 electrically coupled to and configured to deliver electrical power to the first and second lens electrodes 134, 136. The first and second lens electrodes 134, 136 can be at least semi-transparent (e.g., substantially transparent) to visible light.

In an embodiment, the switchable lens 104 can be modified to switch between a first focal length and at least a second focal length. For example, in a first, ground state, the electro-optical material of the switchable lens 104 can exhibit a first index of refraction and a first focal length. The ophthalmic device 100 can apply a first electrical bias to the switchable lens 104 such that the electro-optical material exhibits a second, activated state. In the second, activated state, the electro-optical material of the switchable lens 104 can exhibit a second index of refraction and a second focal length. In an embodiment, the switchable lens 104 can be modified to switch between three or more focal lengths. For example, the switchable lens 104 can be configured to exhibit a first focal length, a second focal length that is greater than the first local length, and one or more intermediate focal lengths having a magnitude between the first focal length and the second focal length. The electro-optical material can exhibit the one or more intermediate focal lengths when one or more electrical biases are applied to the switchable lens 104 that are different (e.g., exhibit different intensities) than the first electrical bias.

As previously discussed, the ophthalmic device 100 can include the at least one first sensor 106. The first sensor 106 can be at least partially disposed in (e.g., encapsulated by, embedded in) the ophthalmic device 100. For example, at least a portion (e.g., at least one electrode) of the first sensor 106 can be disposed in an outer periphery of the ophthalmic device 100 (e.g., in the haptics 118). The first sensor 106 can be configured to sense one or more EMG signals. In particular, the first sensor 106 can be configured to sense EMG signals associated with (e.g., at least partially generated by) the ciliary muscle 110. However, in an embodiment, the first sensor 106 can also sense EMG signals from the iris 122, one or more of the rectus muscles, or other muscular activities.

As previously discussed, the first sensor 106 includes the first electrode 112 and the second electrode 114. The first and second electrodes 112, 114 are disposed in or on the ophthalmic device 100 and configured to sense the EMG signals associated with the ciliary muscle 110. In an embodiment, at least one of the first or second electrodes 112, 114 can be disposed in a portion of the ophthalmic device 100 at least proximate to the ciliary muscle 110 when the ophthalmic device 100 is placed in or on the eye 102. For example, at least one of the first or second electrodes 112, 114 can be disposed in a radially outermost portion of the ophthalmic device 100. In an embodiment, at least one of the haptics 118 can contact the ciliary muscle 110. In such an embodiment, at least one of the first or second electrodes 112, 114 can be disposed on a surface of the haptic 118 that contacts the ciliary muscle 110.

As previously discussed, the first and second electrodes 112, 114 can sense EMG signals associated with a body part other than the ciliary muscle 110. For example, the first and second electrodes 112, 114 can sense EMG signals associated with the iris 122. In an embodiment, the first and second electrodes 112, 114 can be disposed in or on the ophthalmic device 100 to increase a percentage of the sensed EMG signals associated with the ciliary muscle 110. For example, the first and second electrodes 112, 114 can be disposed in or on the ophthalmic device 100 to increase a distance from the first or second electrodes 112, 114 to the ciliary muscle 110 compared to a distance from the first or second electrodes 112, 114 to the iris 122 (hereafter called the "comparative distance"). The comparative distance can be at least about 0.5 mm, such as about 0.5 mm, about 0.75 mm, about 1 mm, about 1.5 mm, about 2 mm, about 2.5 mm, about 3 mm, about 4 mm, about 5 mm, about 6 mm, about 7 mm, about 8 mm, about 9 mm, about 10 mm, about 15 mm, about 20 mm, or about 25 mm, including ranges with endpoints having any of the provided comparative distances. In an embodiment, the comparative distance can greater than about 25 mm. Increasing the comparative distance can increase the percentage of the EMG signals sensed by the first and second electrodes 112, 114 associated with the ciliary muscle 110.

In an embodiment, the first and second electrodes 112, 114 can be spaced (e.g., center-to-center spacing) at least about 0.5 mm from each other, such as about 0.5 mm, 0.75 mm, 1 mm, 1.25 mm, 1.5 mm, 2 mm, 3 mm, 4 mm, 5 mm, 7.5 mm, 1 cm, 2 cm, 3 cm, 4 cm, or 5 cm, including ranges with endpoints having any of the provided spacings. In an embodiment, the first and second electrodes 112, 114 can be spaced less than about 0.5 mm or greater than 5 cm from each other. The spacing between the first and second electrodes 112, 114 affect the operation of the first sensor 106. Increasing the spacing between the first and second electrodes 112, 114 can increase an amplitude of the EMG signals sensed. In an embodiment, decreasing the spacing between the first and second electrodes 112, 114 can decrease the cross-talk (e.g., EMG signals not associated with the ciliary muscle 110) sensed by the first and second electrodes 112, 114.

In an embodiment, at least one of the first and second electrodes 112, 114 includes an electrically conductive surface. The electrically conductive surface can exhibit a generally circular shape, a generally bar-like shape, wire-like shape, or any other suitable shape. In one or more embodiments, the electrically conductive surface can exhibit a cross-sectional dimension that is greater than about 0.25 mm, such as 0.25 mm, 0.5 mm, 0.75 mm, 1 mm, 1.25 mm, 1.5 mm, 2 mm, 3 mm, 4 mm, 5 mm, 7.5 mm, 1 cm, or 2 cm, including ranges with endpoints having any of the provided dimensions. Increasing the cross-sectional dimension of the electrically conductive surface can increase the portions of the ciliary muscle 110 sensed by the first sensor 106. However, increasing the cross-sectional dimension of the electrically conductive surface can increase the cross-talk sensed by the first sensor 106.

In an embodiment, the first sensor 106 can include one or more additional electrodes (not shown) that are also configured to sense the EMG signals. For example, the additional electrodes can be positioned and configured to sense EMG signals associated with the ciliary muscle 110. The additional electrodes can be similar to any of the first or second electrode 112, 114 disclosed herein.

In an embodiment, the first sensor 106 can include at least one reference electrode 140 configured to sense one or more background signals. The background signals can include any signal sensed by the first, second, or reference electrodes 140 that are not the EMG signals associated with the ciliary muscle 110. For example, the background noise can be noise (e.g., ambient electrical potentials) or EMG signals associated with the iris 122 or the medial rectus muscle.

The reference electrode 140 can be configured to sense more of the background signals and less of the EMG signals associated with the ciliary muscle 110 than the first or second electrodes 112, 114. For example, the reference electrode 140 can be positioned within or near the switchable lens 104 such that the reference electrode 140 is relatively more spaced from the ciliary muscle 110 than the first and second electrodes 112, 114. In an embodiment, the reference electrode 140 can be positioned to be proximate to, contact, or at least partially in the iris 122 of the eye 102. In an embodiment, the reference electrode 140 can be disposed in or on a portion of the ophthalmic device 100 to minimize the comparative distance between the reference electrode 140 and the ciliary muscle 110 compared to the distance between the reference electrode 140 and the iris 122 (e.g., the comparative distance is less than 0.5 mm, less than 0.25 mm, less than 0.1 mm). In an embodiment, the reference electrode 140 can be positioned within the anterior chamber 142, the posterior chamber 144, or the vitreous body 146 of the eye 102. The controller 116 can use one or more characteristics sensed by the reference electrode 140 to at least partially exclude (e.g., subtract) background signals sensed by the first and second electrodes 112, 114. In an embodiment, the reference electrode 140 can be omitted.

In an embodiment, the at least one first sensor 106 can transmit one or more first sensing signals responsive to sensing the EMG signals. For example, the first sensor 106 can transmit the first sensing signals responsive to sensing the EMG signals (e.g., the EMG signals associated with the ciliary muscle 110) sensed by the first and second electrodes 112, 114 or the background signals sensed by the reference electrode 140. The first sensing signals can include at least one of the signals sensed by the first sensor 106 encoded therein. In an embodiment, the first sensor 106 transmits the first sensing signals to the controller 116. For example, the first sensor 106 can transmit the first sensing signals to the controller 116 using a hardwired connect, such as electrical wires or traces. In an embodiment, the first sensor 106 can transmit the first sensing signals to a device external to the ophthalmic device 100 (e.g., a mobile device, a computer, another ophthalmic device, etc.). The first sensor 106 can be configured to transmit the first sensing signals to the device external to the ophthalmic device 100 either directly (e.g., the first sensor 106 includes a transceiver) or indirectly (e.g., via transceiver 152 of the controller 116).

As previously discussed, the ophthalmic device 100 includes at least one second sensor 108. The second sensor 108 can be at least partially disposed in (e.g., encapsulated by) or on the ophthalmic device 100. For example, the second sensor 108 can be at least partially disposed in one of the haptics 118, the switchable lens 104, or another component of the ophthalmic device 100. For example, the second sensor 108 can be at least partially disposed in the same haptic 118 as the first sensor 106 or another one of the haptics 118.

The second sensor 108 can be configured to sense one or more characteristics. The one or more characteristics sensed by the second sensor 108 can be at least one of one or more accelerations of the eye 102, one or more electromagnetic signals, one or more magnetic fields, or other suitable characteristic. The one or more characteristics sensed by the second sensor 108 can be used, either by themselves or in conjunction with characteristics sensed by the first sensor 106, to determine at least one of vergence rotation (e.g., divergence or convergence), saccade, duction, conjugate rotation of two eyes in the same direction, pursuit eye movement, or other suitable characteristic.

The second sensor 108 is distinct from the first sensor 106. For example, the second sensor 108 can include a sensor that is a different type of sensor than the first sensor 106. In an embodiment, the second sensor 108 can be configured to sense one or more characteristics that differ from EMG signals. In an embodiment, the second sensor 108 can be spaced from the first sensor 106 and is substantially similar to the first sensor 106 (e.g., second sensor 908 of FIG. 9).

In an embodiment, the second sensor 108 can include at least one accelerometer. The accelerometer can be configured to sense accelerations (e.g., movements) of the eye 102 (e.g., eye rotation). The accelerations sensed by the accelerometer can be caused by rotation of the eye 102 and can determine vergence rotation. For example, the accelerometer can be configured to sense when the eye 102 rotates at least one of inwardly (e.g., towards the nose), outwardly (e.g., towards the ears), upwardly (e.g., towards the forehead), or downwardly (e.g., towards the mouth). The accelerometer can include at least one out-of-plane accelerometer, a single in-plane accelerometer, or a plurality of in-plane accelerometers.

As will be discussed later, in one or more embodiments, the second sensor 108 can include a sensor that differs from the accelerometer. For example, the second sensor 108 can include at least one photodetector (e.g., second sensor 508 of FIGS. 5A-5B), at least one magnetic sensor (e.g., second sensor 608, 708 of FIGS. 6-8), at least one sensor configured to sense EMG signals (e.g., second sensor 908 of FIG. 9), or another suitable sensor.

In an embodiment, the second sensor 108 can transmit one or more second sensing signals responsive to sensing the one or more characteristics. For example, the second sensor 108 can transmit the second sensing signals responsive to sensing one or more accelerations of the eye 102, one or more electromagnetic signals, one or more magnetic fields, etc. The second sensing signals can include at least one of characteristic sensed by the second sensor 108 encoded therein. In an embodiment, the second sensor 108 transmits the second sensing signals to the controller 116. For example, the second sensor 108 can transmit the second sensing signals to the controller 116 or to a device external to the ophthalmic device 100 (e.g., a computer, a mobile device, another ophthalmic device, etc.).

In an embodiment, the ophthalmic device 100 can include one or more physiological sensors (not shown). For example, the physiological sensors can be disposed in or on at least one of the haptics 118. The physiological sensors can be configured to sense one or more physiological characteristics. The physiological characteristics can include characteristics that are not used to determine whether the one or more electromyography signals sensed by the first sensor 106 was associated with the ciliary muscle 110. The physiological sensors can include a glucose sensor, a heart rate sensor, a pulse oximeter, a temperature sensor, a moisture sensor, or another suitable physiological sensor. The physiological sensors can be configured to output one or more physiological signals responsive to sensing one or more physiological characteristics. For example, the physiological sensors can transmit the physiological signals to the controller 116 or to a device remote from the ophthalmic device 100. For example, the physiological sensor can transmit (e.g., via transmitter 152) the physiological signals to an implanted or implantable device, a wearable device (e.g., insulin pump), or a computer or network that includes patient records.

As discussed above, the ophthalmic device 100 can include the at least one power source 138. The power source 138 can include a battery (e.g., microbattery), a capacitor, an energy harvester (e.g., piezoelectric, solar cell, etc.), or another suitable device. The power source 138 can be operably coupled to and configured to deliver power (e.g., electrical power) to the one or more components of the ophthalmic device 100. For example, the power source 138 can controllably deliver electrical power to the first and second lens electrodes 134, 136 such that the switchable lens 104 can controllably change the focal length thereof. In another example, the power source 138 can deliver electrical power to the first or second sensors 106, 108.

The controller 116 is operably (e.g., communicably) coupled to one or more components of the ophthalmic device 100. For example, the controller 116 is operably coupled to at least one of the switchable lens 104, the first sensor 106, the second sensor 108, the power source 138, the physiologic sensor, or another component of the ophthalmic device 100. The controller 116 can include control electrical circuitry configured to at least partially control the operation of the one or more components of the ophthalmic device 100. For example, the controller 116 can include at least one memory storage medium 148, at least one processor 150 (e.g., processing electrical circuitry) operably coupled to the memory storage medium 148, and the transceiver 152. In an embodiment, the controller 116 is communicably coupled to the first and second sensors 106, 108 such that the controller 116 can receive the first and second sensing signals. The controller 116 can be configured to direct the at least one switchable lens to selectively switch the focal length thereof responsive to receiving the first and second sensing signals. In an embodiment, the controller 116 can direct the power source 138 to deliver electrical power to the first and second lens electrodes 134, 136 responsive to receiving the first and second sensing signals. In an embodiment, the controller 116 can direct the first or second sensors 106, 108 to sense EMG signals or other characteristics.

Figure 11:
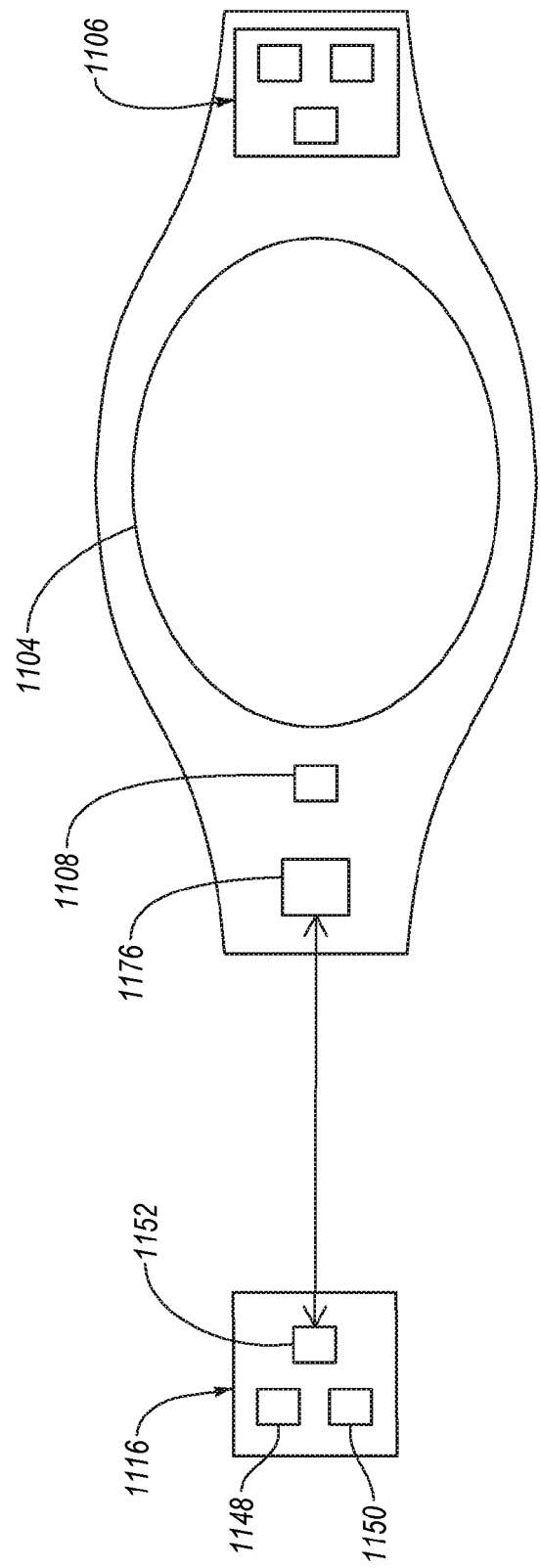
FIG. 11 is a schematic illustration of an ophthalmic system that includes an ophthalmic device and a controller that is spaced from the ophthalmic device, according to an embodiment.

In an embodiment, at least a portion of the controller 116 can be at least partially disposed in or on the ophthalmic device 100. For example, the controller 116 can be encapsulated by at least a portion of the switchable lens 104 or the haptics 118. In an embodiment, at least a portion of the controller 116 can be distinct (e.g., spaced and remote) from the ophthalmic device 100 (FIG. 11).

The memory storage medium 148 can be physically disposed in the controller 116 or separate from and communicably coupled to the controller 116. The at least one memory storage medium 148 can include any non-transitory memory storage medium, such as a hard-disk drive, a solid state memory device, a flash drive, or the like. The at least one memory storage medium 148 can include one or more of program instructions for the at least one processor 150, data from the first or second sensors 106, 108 (e.g., the first or second sensing signals that are currently or previously received by the controller 116), one or more comparative algorithms discussed herein used to determine when the controller 116 should direct the switchable lens 104 to selectively switch the focal length thereof (e.g., the algorithms can compare the first and second sensing signals to determine a vergence rotation of the eye 102), a history of the ophthalmic device 100 (e.g., when the switchable lens 104 switched the focal length thereof), look-up tables, one or more databases, or ophthalmic system diagnostic statuses (e.g., current and past statuses of any component of the ophthalmic device 100).

The at least one processor 150 can be operably coupled to the memory storage medium 148. The processor 150 is configured to access and read the memory storage medium 148. The processor 150 can be configured to receive sensor data including the signals and characteristics sensed by the first and second sensors 106, 108. The at least one processor 150 is configured to direct the at least one switchable lens 104 to selectively switch the focal length thereof.

The processor 150 can be configured to determine whether the one or more EMG signals sensed by the first sensor 106 are at least partially associated with the ciliary muscle 110. For example, the processor 150 can be configured to analyze the one or more EMG signals sensed by the first sensor 106. Analyzing the one or more EMG signals can include using the background signals sensed by the reference electrode 140 to subtract at least some of the noise from the EMG signals sensed by the first and second electrodes 112, 114. Analyzing the one or more EMG signals can include matching the sensed EMG signals with EMG signals patterns generally associated with the ciliary muscle 110, the iris 122, or another source. However, in many circumstances, the processor 150 may not distinguish between the EMG signals associated with the ciliary muscle 110, the iris 122, or another source because the first and second electrodes 112, 114 are proximate to both the ciliary muscle 110 and the iris 122 due to the limited size of the ophthalmic device 100. Similarly, in some applications, the reference electrode 140 cannot be placed within a neutral location due to the limited size of the ophthalmic device 100. For example, the reference electrode 140 can detect EMG signals associated with the ciliary muscle 110 due to the proximity of the reference electrode 140 to the ciliary muscle 110.

The processor 150 can be configured to compare the first and second sensing signals to determine whether the EMG signals sensed by the first electrode 112 were at least partially associated with the ciliary muscle 110. For example, the processor 150 can compare the first and second sensing signals to determine whether one of, both, or none of the first and second sensors 106, 108 sensed EMG signals or characteristics, respectfully. In an embodiment, the processor 150 can compare the first and second sensing signals to determine whether one of, both, or none of the first and second sensors 106, 108 sensed a change in EMG signals or characteristics, respectfully.

In an embodiment, the processor 150 can compare the first and second sensing signals to determine a likelihood that the EMG signals sensed by the first sensor 106 are associated with the ciliary muscle 110 or other muscular activity. The controller 116 can direct the switchable lens 104 to selectively switch the focal length thereof when the processor 150 determines that the likelihood that the EMG signals sensed by the first sensor 106 are associated with the ciliary muscle 110 are above a threshold level. In an embodiment, the threshold level can be preselected. In an embodiment, the threshold level can be varied. For example, the threshold level can be varied based on a time of day, an intensity of the EMG signals sensed by the first sensor 106, an intensity of the characteristics sensed by the second sensor 108, or the characteristic sensed by the second sensor 108 (e.g., electromagnetic signals, magnetic fields, etc.). In an embodiment, the threshold level can be when the likelihood that the EMG signals sensed by the first sensor 106 are associated with the ciliary muscle 110 are at or above 1%, 10%, 20%, 30%, 40%, 50%, 60%, 70%, 75%, 80%, 85%, 90%, 95%, 98% 99%, 99.9%, or 99.99%, including ranges with endpoints having any of the provided percentages. The controller 116 can direct the switchable lens 104 to selective switch the focal length thereof at least partially based on the likelihood that the EMG signals are associated with the ciliary muscle 110.

The EMG signals sensed by the first sensor 106 can be partially generated by the ciliary muscle 110. For example, changing focus from a bright or close object to a dark or remote object can cause the ciliary muscle 110 and the iris 122 to both generate EMG signals. In an embodiment, the processor 150 can compare the first and second sensing signals to determine a percentage of the EMG signals sensed by the first sensor 106 associated with the ciliary muscle 110. For example, the processor 150 can compare an intensity or a quantity of the EMG signals to an intensity or quantity of the characteristics sensed by the second sensor 108 to determine the percentage of the EMG signals associated with the ciliary muscle 110. The controller 116 can direct the switchable lens 104 to selective switch a focal length thereof at least partially based on the percentage of the EMG signals generated by the ciliary muscle 110.

In an embodiment, the processor 150 can compare the first and second sensing signals to determine a vergence rotation between the eye 102 and the other eye of the individual ("vergence rotation"). The vergence rotation can determine an apparent object distance (e.g., the distance from the individual to the object on which the individual's eyes are attempting to focus). In an embodiment, the controller 116 can direct the switchable lens 104 to selectively switch a focal length thereof at least partially based on the vergence rotation. In an embodiment, the controller 116 can use the vergence rotation to determine which focal length the switchable lens 104 selectively switches between. For example, the switchable lens 104 can be switchable between a first, second, and third focal length.

In an embodiment, the processor 150 can direct the switchable lens 104 to selectively switch the focal length thereof when the first sensor 106 senses the EMG signals and the second sensor 108 senses a change in the characteristics sensed thereby (e.g., the changes in the sensed characteristics indicate vergence rotation or a change in apparent object distance). For example, the processor 150 can determine that the EMG signals sensed by the first sensor are associated with the ciliary muscle 110 when the first sensor 106 senses the EMG signals and the second sensor senses a change in the characteristics sensed thereby. In an embodiment, the processor 150 can direct the switchable lens 104 to maintain the focal length thereof when only one of the first sensor 106 senses the EMG signals or the second sensor 108 senses a change in the characteristics sensed thereby. For example, the processor 116 can determine that the EMG signals sensed by the first sensor 106 are not associated with the ciliary muscle 110 (e.g., the EMG signals are generated by the iris 122) when the second sensor 108 does not also sense a change in the characteristics sensed thereby. In another example, the processor 116 can determine that the characteristics sensed by the second sensor 108 do not indicate vergence rotation or a change in apparent object distance when the first sensor 106 does not sense EMG signals.

In an embodiment, the second sensor 108 can include at least one accelerometer configured to sense an acceleration of the eye 102. The processor 150 can compare the first sensing signals (e.g., the EMG signals sensed by the first sensor 106) with the second sensing signals (e.g., the accelerations sensed by the second sensor 108) to determine whether the ciliary muscle 110 is associated with the EMG signals, the vergence rotation, or the apparent object distance. For example, the first sensing signals can indicate that the first sensor 106 sensed one or more EMG signals and the second sensing signals can indicated that the second sensor 108 sensed inward or outward rotations of the eye 102. In such an example, the processor 150 can determine at least one of a likelihood that the EMG signals are associated with the ciliary muscle 110, a percentage of the EMG signals generated by the ciliary muscle 110, a vergence rotation, or an apparent object distance. In an embodiment, the first sensing signals can indicate that the first sensor 106 sensed one or more EMG signals and the second sensing signals can indicate that the second sensor 108 sensed substantially no inward or outward rotations of the eye 102 (e.g., the second sensor 108 sensed no rotation, substantially only upward rotation, substantially only downward rotation). In such an example, the processor 150 can determine from the first and second sensing signals that the EMG signals were likely not associated with the ciliary muscle 110. In an embodiment, the first sensing signals can indicate that the first sensor 106 sensed substantially no EMG signals and the second sensing signals can indicate that the second sensor 108 sensed inward or outward rotations of the eye 102. In such an embodiment, the processor 150 can determine from the first and second sensing signals that the EMG signals were likely not associated with the ciliary muscle 110 and, consequently, the controller 116 does not direct the switchable lens 104 to alter a focal length thereof.

The controller 116 can include the at least one transceiver 152 or the transceiver 152 can be spaced from and communicably coupled to the controller 116. The transceiver 152 can be configured to communicate with an entity (not shown). The entity can include one or more of a computer, a mobile device, a network, another device implanted or implantable into the individual, a device that the individual can wear, etc. For example, the transceiver 152 can be configured to communicate with an insulin pump when the physiological sensors include a glucose sensor.

In an embodiment, the entity can at least partially control the operation of one or more components of the ophthalmic device 100. For example, the entity can relay one or more instructions, one or more programs, or other information to the controller 116. In an embodiment, the controller 116 can relay information (e.g., the first or second sensing signals, status of the ophthalmic device 100, status of one or more individual components of the ophthalmic device 100, etc.) to the entity.

In an embodiment, the entity allows the ophthalmic device 100 to communicate with the individual or a third party (e.g., medical professional). For example, the entity can include a user interface. The user interface can include one or more output devices (e.g., screen, chime, or haptic indicator) and one or more input devices (e.g., keyboard, buttons, levers, switches, or dials). The user interface can be configured to output information to the individual or third party (e.g., information transmitted from the ophthalmic device 100) and accept input from the individual or the third party (e.g., one or more instructions, one or more programs, etc.). For example, the individual can use the user interface to manually change the focal length of the switchable lens 104.

In an embodiment, at least a portion of the ophthalmic device 100 can be hermetically sealed. For example, at least one of the switchable lens 104, at least a portion of the first sensor 106 (e.g., at least one of the first, second, or ground electrodes 112, 114, 140), the second sensor 108, at least a portion of the controller 116 (e.g., at least one of the memory storage medium 148, the processor 150, or the first transceiver), at least one of the haptics 118, the power source 138, the physiological sensors, etc. can be hermetically sealed within the ophthalmic device 100. For example, in one or more embodiments, the ophthalmic device 100 can be highly miniaturized, self-contained and can involve two or more components.

Figure 2:
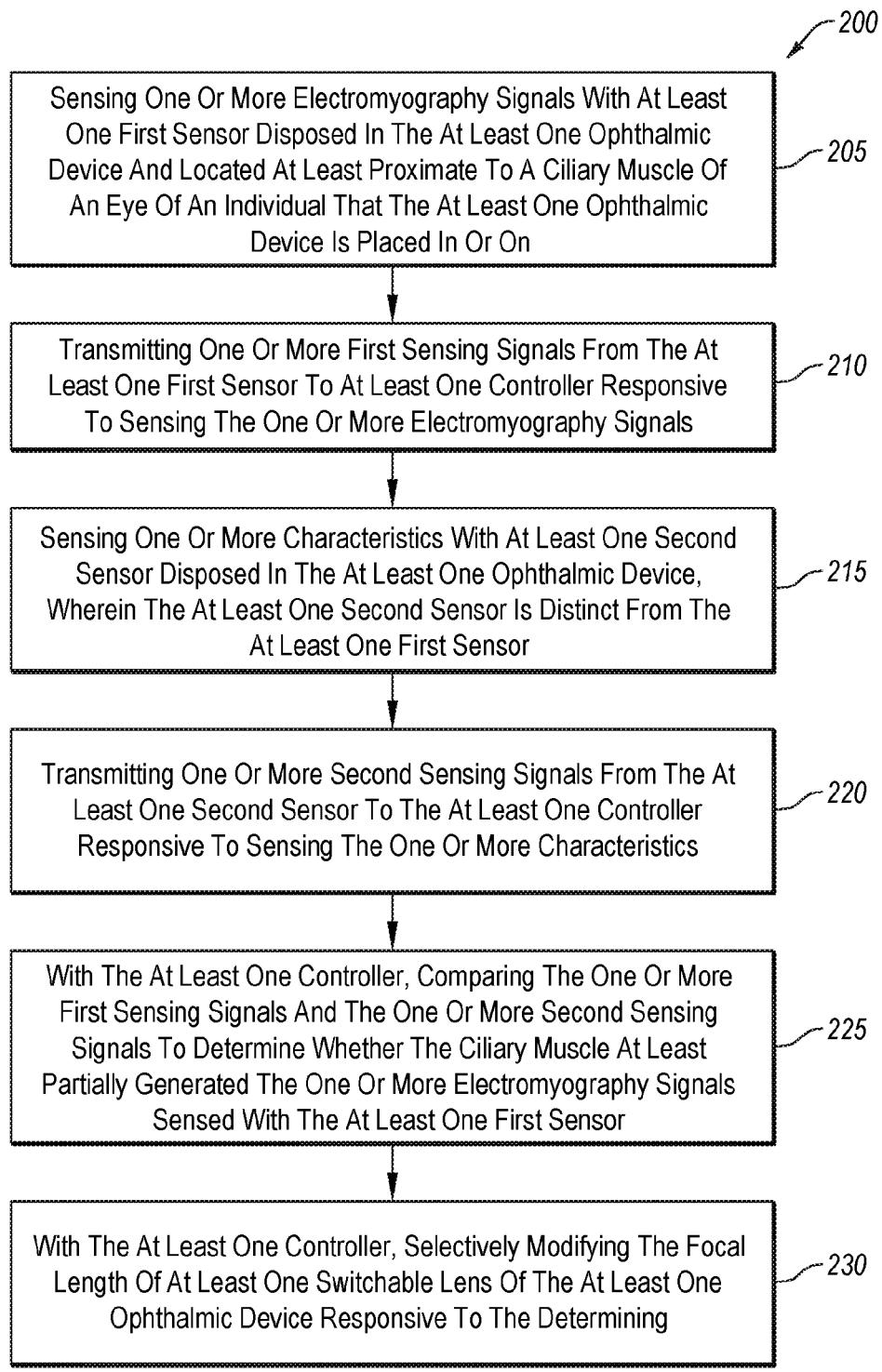
FIG. 2 is a flow diagram of a method of using the ophthalmic device of FIGS. 1A-1B, according to an embodiment.

FIG. 2 is a flow diagram of a method 200 of using the ophthalmic device 100 of FIGS. 1A-1B, according to an embodiment. In an embodiment, some acts of method 200 can be split into a plurality of acts, some acts can be combined into a single act, and some acts can be omitted. Also, it is understood that additional acts can be added to the method 200. Except as otherwise disclosed herein, the acts of method 200 can be used with any of the ophthalmic devices and ophthalmic systems disclosed herein.

Act 205 includes sensing one or more EMG signals with the at least one first sensor 106 of the at least one ophthalmic device 100 and located at least proximate to a ciliary muscle 110 of an eye 102 of an individual that the at least one ophthalmic device 100 is placed in or on. Sensing the one or more EMG signals can include sensing an EMG signal (e.g., electrical potential) using the first, second, and reference electrodes 112, 114, 140. For example, the first and second electrodes 112, 114 can sense the EMG signals or a change in the EMG signals. In an embodiment, sensing the EMG signals can include sensing EMG signals associated with the ciliary muscle 110 or other muscular activity (e.g., muscular activity of the iris 122). In an embodiment, sensing the EMG signals can include sensing one or more background signals with the reference electrode 140. The first sensor 106 can sense the EMG signals responsive to directions from the controller 116.

Act 210 includes transmitting one or more first sensing signals from the at least one first sensor 106 to at least one controller 116 responsive to sensing the one or more EMG signals. For example, transmitting the first sensing signals can include transmitting EMG signals sensed by the first and second electrodes 112, 114, background signals sensed by the reference electrode 140, or changes in the signals sensed by the first, second, or reference electrodes 112, 114, 140. In an embodiment, transmitting the first sensing signals can include transmitting that the first sensor 106 sensed no EMG signals or changes in the EMG signals.

Act 215 includes sensing one or more characteristics with the at least one second sensor 108 of the at least one ophthalmic device 100, wherein the at least one second sensor 108 is distinct from the at least one first sensor 106. Sensing the characteristics can include sensing an existence of or change in at least one of the characteristics. Sensing the characteristics can include sensing the characteristics with any of the second sensors described herein. For example, the second sensor 108 can include at least one accelerometer and sensing the characteristics can include sensing one or more accelerations of the eye 102 or at least a portion of the ophthalmic device 100. In an embodiment, the second sensor 108 can include at least one photodetector and sensing the characteristics can include sensing one or more electromagnetic signals. In an embodiment, the second sensor 108 can include at least one magnetic field sensor and sensing the characteristics can include sensing one or more magnetic fields. In an embodiment, the second sensor 108 can sense the characteristics responsive to direction from the controller 116. The second sensor 108 can sense the characteristics substantially simultaneously with the first sensor 106 sensing the EMG signals.

Act 220 includes transmitting one or more second sensing signals from the at least one second sensor 108 to the at least one controller 116 responsive to sensing the one or more characteristics. For example, transmitting the second sensing signals can include transmitting signals indicating that the second sensor 108 sensed one or more accelerations, one or more electromagnetic signals, one or more magnetic fields, a change in the one or more characteristics, or another characteristic. In an embodiment, transmitting the second sensing signals can include transmitting signals indicating that the second sensors 108 did not sense the characteristics or sensed no change in the characteristics. The second sensor 108 can transmit the second sensing signals substantially simultaneously with the first sensor 106 transmitting the first sensing signals.

Act 225 includes, with the at least one controller 116, comparing the one or more first sensing signals and the one or more second sensing signals to determine whether the ciliary muscle 110 at least partially generated the one or more EMG signals sensed with the at least one first sensor 106. Comparing the first and second sensing signals can include comparing the intensity of the EMG signals to the intensity of the characteristics, comparing a change (or lack thereof) in the EMG signals to a change (or lack thereof) in the characteristics, using the background signals sensed by the reference electrode 140 to subtract a portion of the EMG signals sensed by the first and second sensor 106, 108, etc. Comparing the first and second sensing signals can also include, with the processor 150, determining a likelihood that the EMG signals are associated with the ciliary muscle 110 or other muscular activity, if the likelihood is greater than a threshold value, a percentage of the EMG signals associated with the ciliary muscle 110 or other muscular activity, a vergence rotation, an apparent object distance, etc. Comparing the first and second sensing signals can also include, with the processor 150, distinguishing the EMG signals associated with the ciliary muscle 110 from the EMG signals associated with other muscular activity.

Act 230 includes, with the at least one controller 116, selectively modifying the focal length of at least one switchable lens 104 of the at least one ophthalmic device 100 responsive to act 225 of determining. For example, the controller 116 can direct the power source 138 to deliver power to or remove power from the switchable lens 104 to selectively switch the focal length of the switchable lens 104. In an embodiment, the controller 116 can direct the switchable lens 104 to selectively switch the focal length thereof from a first focal length to a second focal length. In an embodiment, the controller 116 can direct the switchable lens 104 to selectively switch the focal length thereof from a first focal length to a second focal length or at least one additional focal length.

In an embodiment, the method 200 can include transmitting one or more command signals from the controller 116 to another component of the ophthalmic device 100. The command signals can include directives to selectively switch the focal length of the switchable lens 104, sense the one or more EMG signals with the at least one first sensor 106, sense the one or more characteristics with the at least one second sensor 108, etc. For example, the controller 116 can transmit the one or more command signals to the switchable lens 104, the first sensor 106, the second sensor 108, the power source 138, or another component of the ophthalmic device 100.

In an embodiment, the method 200 can include transmitting and receiving one or more signals between the controller 116 and an entity. For example, the controller 116 can transmit one or more information signals (e.g., the first and second sensing signals, status updates, etc.) to the entity. For example, the entity can transmit one or more instructions (e.g., command signals) or one or more programs to the controller 116.

In an embodiment, at least a portion of the controller 116 can be positioned remote from the ophthalmic device 100. In such an embodiment, the method 200 can include transmitting the first and second sensing signals to the controller 116 from the ophthalmic device 100. In such an embodiment, the method 200 can include transmitting one or more command signals from the controller 116 to the ophthalmic device 100.

Figure 3:
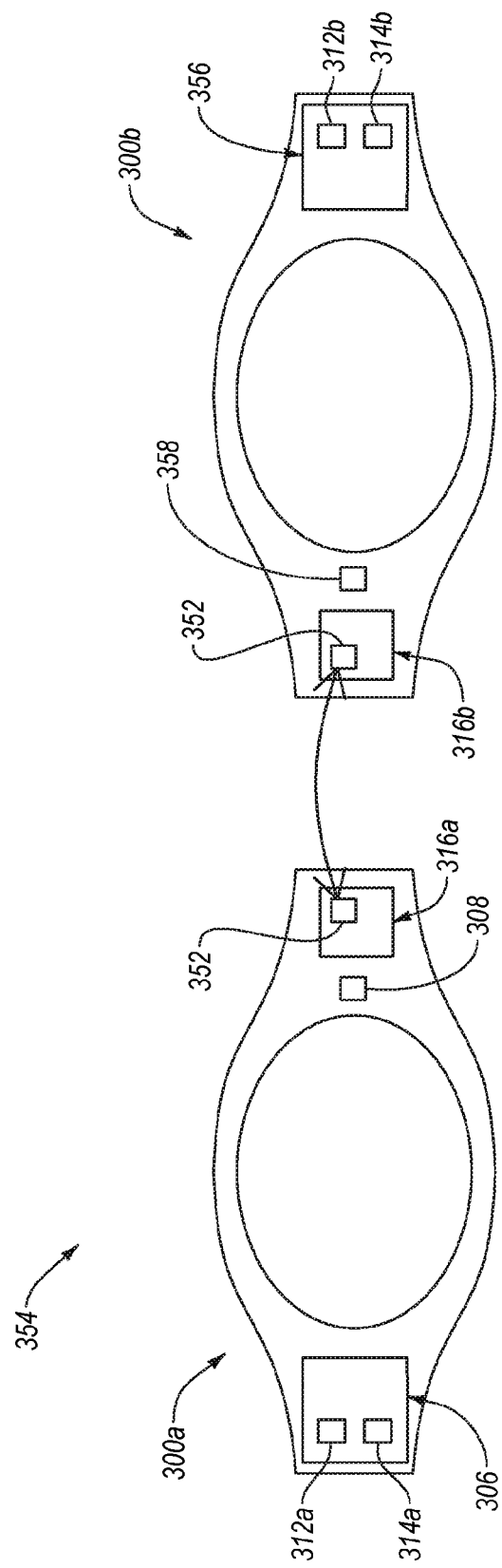
FIG. 3 is a schematic illustration of an ophthalmic system that includes first and second ophthalmic devices, according to an embodiment.

FIG. 3 is a schematic illustration of an ophthalmic system 354 that includes first and second ophthalmic devices 300a, 300b, according to an embodiment. Except as otherwise described herein, the first and second ophthalmic devices 300a, 300b and their materials, components, or elements can be similar to or the same as the ophthalmic device 100 (FIGS. 1A-1B) and its respective materials, components, or elements. For example, the first and second ophthalmic devices 300a, 300b can include at least one switchable lens 304. The ophthalmic system 354 (e.g., the first and second ophthalmic devices 300a, 300b) or its materials, components, or elements can be used in any of the ophthalmic devices or ophthalmic systems disclosed herein.

The first ophthalmic device 300a can be configured to be disposed within a first eye of an individual (not shown). The second ophthalmic device 300b can be configured to be disposed within a second eye of the individual (e.g., the other eye, not shown). In an embodiment, each of the first and second ophthalmic devices 300a, 300b can include a transceiver 352 configured to communicably couple the first and second ophthalmic devices 300a, 300b together.

The first ophthalmic device 300a can be substantially similar to the ophthalmic device 100 (FIGS. 1A-1B). For example, the first ophthalmic device 300a can include a first sensor 306 positioned and configured to sense one or more EMG signals. The first sensor 306 includes first and second electrodes 312a, 314a configured to sense the EMG signals. The EMG signals sensed by the first sensor 306 can be associated with a ciliary muscle of the first eye. The first sensor 306 can be configured to transmit one or more first sensing signals responsive to sensing the EMG signals. The first ophthalmic device 300a can also include a second sensor 308 distinct from the first sensor 306 configured to detect one or more characteristics. For example, the second sensor 308 can be configured to detect accelerations, electromagnetic signals, magnetic fields, or EMG signals.

In an embodiment, the second ophthalmic device 300b can include a third sensor 356 at least partially disposed therein or thereon. The third sensor 356 can be substantially similar to the first sensor 106 (FIGS. 1A-1B). For example, the third sensor 356 can include first and second electrodes 312b, 314b positioned and configured to sense one or more EMG signals present in the second eye. For example, the third sensor 356 can be configured to sense EMG signals associated with the ciliary muscle of the second eye. The third sensor 356 can be configured to transmit one or more third sensing signals to one or more devices (e.g., the first or second controller 316a, 316b) responsive to sensing the EMG signals. For example, the third sensor 356 can be configured to transmit the third sensing signals to first controller 316a via the transceivers 352. In an embodiment, the third sensor 356 senses the EMG signals responsive to direction from the first controller or another controller (e.g., second controller 316b, an entity, etc.).

In an embodiment, the second ophthalmic device 300b can include a fourth sensor 358 at least partially disposed therein or thereon. The fourth sensor 358 can be similar to or the same as any of the second sensors disclosed herein (e.g., second sensors 108 of FIGS. 1A-1B). For example, the fourth sensor 358 can be configured to sense one or more characteristics (e.g., accelerations, electromagnetic signals, magnetic fields, EMG signals). The fourth sensor 358 can be configured to transmit one or more fourth sensing signals to one or more devices (e.g., the first or controller 316a, 316b) responsive to sensing the characteristics. For example, the fourth sensor 358 can be configured to transmit the fourth sensing signals to the first controller 316a via the transceivers 352. In an embodiment, the fourth sensor 358 can be configured to sense the characteristics responsive to direction from the first controller 316a or another device (e.g., the second controller 316b, an entity, etc.).

In an embodiment, the second ophthalmic device 300b includes both the third and fourth sensors 356, 358. In an embodiment, the second ophthalmic device 300b includes only one of the third or fourth sensor 356, 358. In an embodiment, the second ophthalmic device 300b does not include the third and fourth sensors 356, 358. In such an embodiment, the focal length of the second ophthalmic device 300b can be selectively switched responsive to comparing the first and second sensing signals.

The first or second ophthalmic device 300a, 300b also include a plurality of controllers 316. For example, the first and second ophthalmic device 300a, 300b can each include at least one first controller 316a and at least one second controller 316b, respectively. For example, the ophthalmic system 354 can include the first controller 316a, the second controller 316b, or both the first and second controllers 316a, 316b. The first and second controller 316a, 316b can be similar to or the same as any of the controllers disclosed herein (e.g., the controller 116 of FIGS. 1A-1B). For example, the first and second controllers 316a, 316b can be at least partially disposed in the first and second ophthalmic devices 300a, 300b, respectively. The first and second controllers 316a, 316b can be operably coupled to one or more components of their respective ophthalmic device or, via the transceivers 352, one or more components of the other ophthalmic device. For example, the first or second controller 316a, 316b can be operably coupled to at least one of the first, second, third, or fourth sensors 306, 308, 356, 358 so the first or second controller 316a, 316b can receive the first, second, third, or fourth sensing signals. In an embodiment, the first and second controllers 316a, 316b can be configured to at least partially control the operation of one or more components their respective ophthalmic device or, via the transceivers 352, one or more components of the other ophthalmic device.

In an embodiment, the first or second controller 316a, 316b is configured to compare at least three of the first, second, third, or fourth sensing signals to determine vergence rotation, apparent object distance, saccade, duction, conjugate rotation of two eyes in the same direction, pursuit eye movement, etc. of the first and second eye. Comparing at least three of the first, second, third, or fourth sensing signals can increase the precision of the comparison performed by the first or second controllers 316a, 316b compared to just analyzing the first and second sensing signals. Additionally, comparing at least three of the first, second, third, or fourth sensing signals can increase the precision of the comparison performed by the first or second controller 316a, 316b in certain situation where both the ciliary muscle and the iris generate the EMG signals, the first and second eyes rotate at unequal rates (e.g., an object passes along a side the individual), etc. For example, the first or second controller 316a, 316b can determine at least one of vergence rotation, apparent object distance, etc., when at least three of the first, second, third, or fourth sensing signals indicate that the first or third sensors 306, 356 sense one or more EMG signals or the second or fourth sensors 308, 358 sense one or more characteristics that indicate vergence rotation. The characteristics that indicate vergence rotation can include inward or outward rotation of the first or second eye, a change in an electromagnetic signal (e.g., changes in an intensity of light, left-to-right or right-to-left movement of an electromagnetic source relative to the eye), a change in a magnetic field, a change of an EMG signal sensed by the second sensor 308, or another suitable characteristic. The first or second controllers 316a, 316b can at least partially control the operation of one or more components of the ophthalmic system 354 responsive to comparing at least three of the first, second, third, or fourth sensing signals.

In an embodiment, the first controller 316a compares the first and second sensing signals and the second controller 316b compares the second and third sensing signals to determine, for example, vergence rotation. The first and second controllers 316a, 316b can compare what each determined. If the determinations of the first and second controller 316a, 316b are substantially the same, the first and second controllers 316a, 316b can at least partially control one or more components of the ophthalmic system 354 without further comparisons or computations. If the determinations of the first and second controller 316a, 316b are different, the first or second controller 316a, 316b can perform further comparisons or computations to remedy the discrepancy. For example, the first or second controller 316a, 316b can compare at least three of the first, second, third, or fourth sensing signals.

Figure 4A:
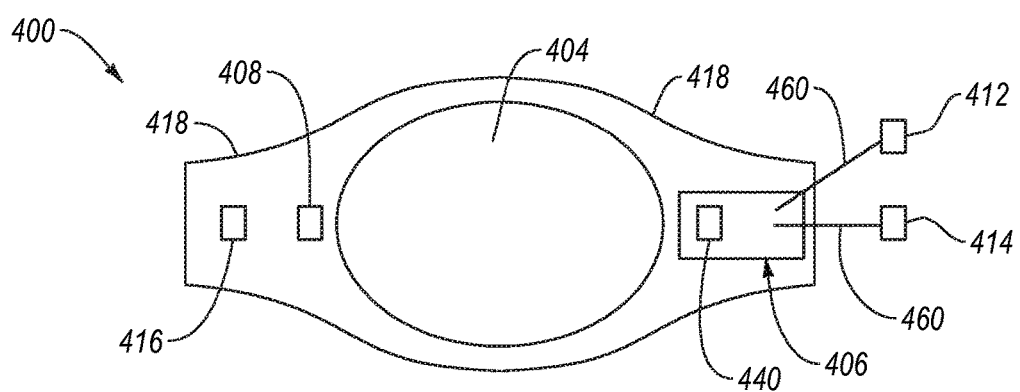
FIG. 4A is a schematic illustration of an ophthalmic device including a first sensor configured to directly contact a ciliary muscle of an eye, according to an embodiment.
Figure 4B:
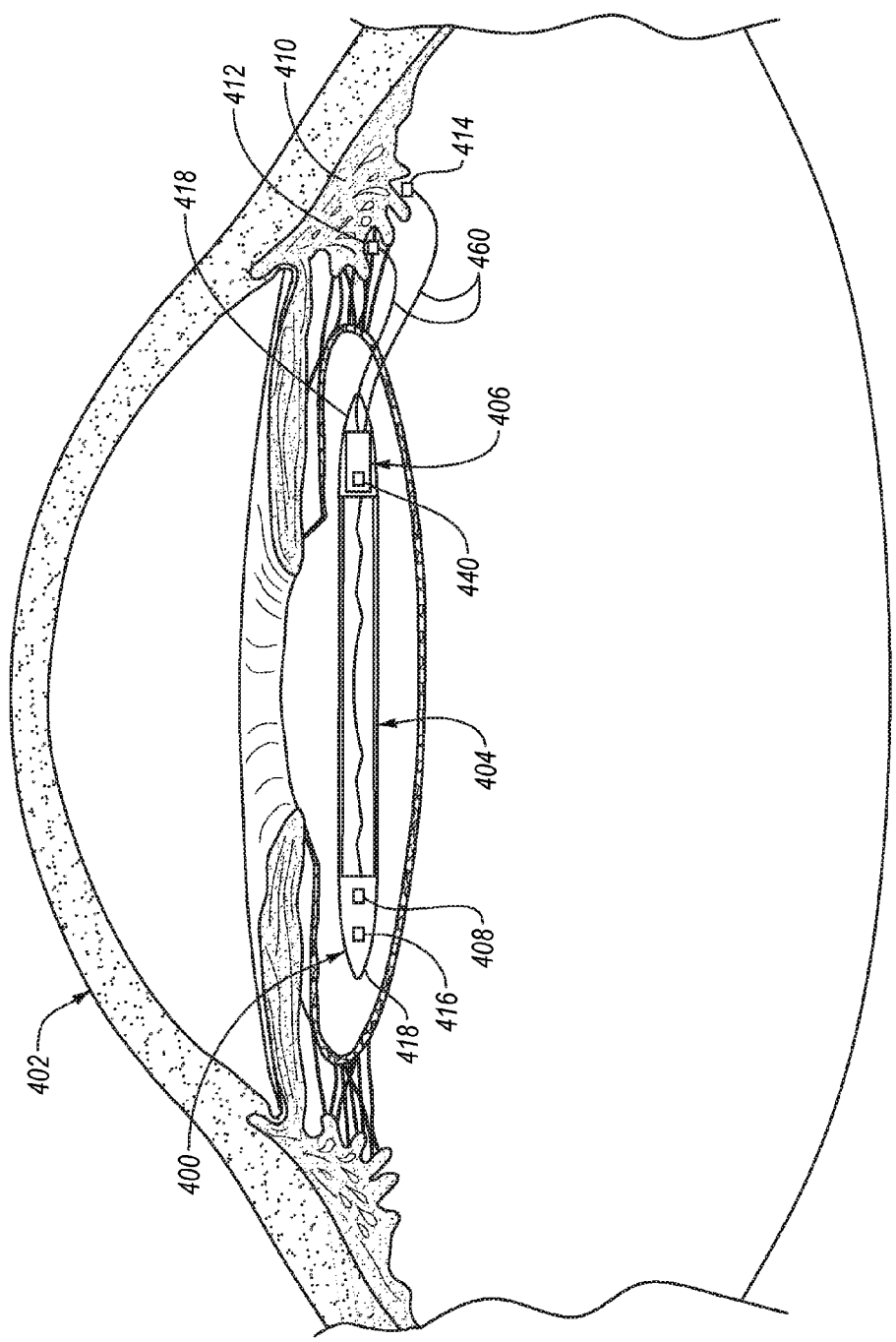
FIG. 4B is a side, cross-sectional view of the ophthalmic device shown in FIG. 4A implanted in the eye.

FIG. 4A is a schematic illustration of an ophthalmic device 400 including a first sensor 406 configured to directly contact a ciliary muscle 410 of an eye 402, according to an embodiment. FIG. 4B is a side, cross-sectional view of the ophthalmic device 400 implanted in the eye 402. Except as otherwise described herein, the ophthalmic devices 400 and its materials, components, or elements can be similar to or the same as the ophthalmic devices 100, 300a-b (FIGS. 1A-1B and 3) and their respective materials, components, or elements. For example, the ophthalmic devices 400 can include at least one switchable lens 404, at least one first sensor 406, at least one second sensor 408, and at least one controller 416. The ophthalmic device 400 or its materials, components, or elements can be used in any of the ophthalmic devices or ophthalmic systems disclosed herein.

The first sensor 406 can include a first electrode 412, a second electrode 414, and, optionally, a reference electrode 440. In an embodiment, at least one of the first or second electrodes 412, 414 is positioned and configured to directly contact the ciliary muscle 410 when the ophthalmic device 400 is placed in or on the eye 402. For example, the first or second electrode 412, 414 can be remote from the switchable lens 404 or the haptics 418. The first or second electrode 412, 414 can be directly coupled to in the ciliary muscle 410 (e.g., disposed on a surface of or embedded in the ciliary muscle 410). In such an embodiment, the ophthalmic device 400 can include at least one coupling mechanism 460 (e.g., cable) that extends from the first sensor 406 to the first or second electrode 412, 414. The coupling mechanism 460 can at least one of physically couple, electrically couple, or communicably couple the first or second electrode 412, 414 to the rest of the first sensor 406 or other component of the ophthalmic device 400. In an embodiment, at least one surface of the haptics 418 can be configured to directly contact the ciliary muscle 410. In such an example, the first or second electrodes 412, 414 can be disposed on the surface of the haptics 418 that directly contacts the ciliary muscle 410.

Figure 5A:
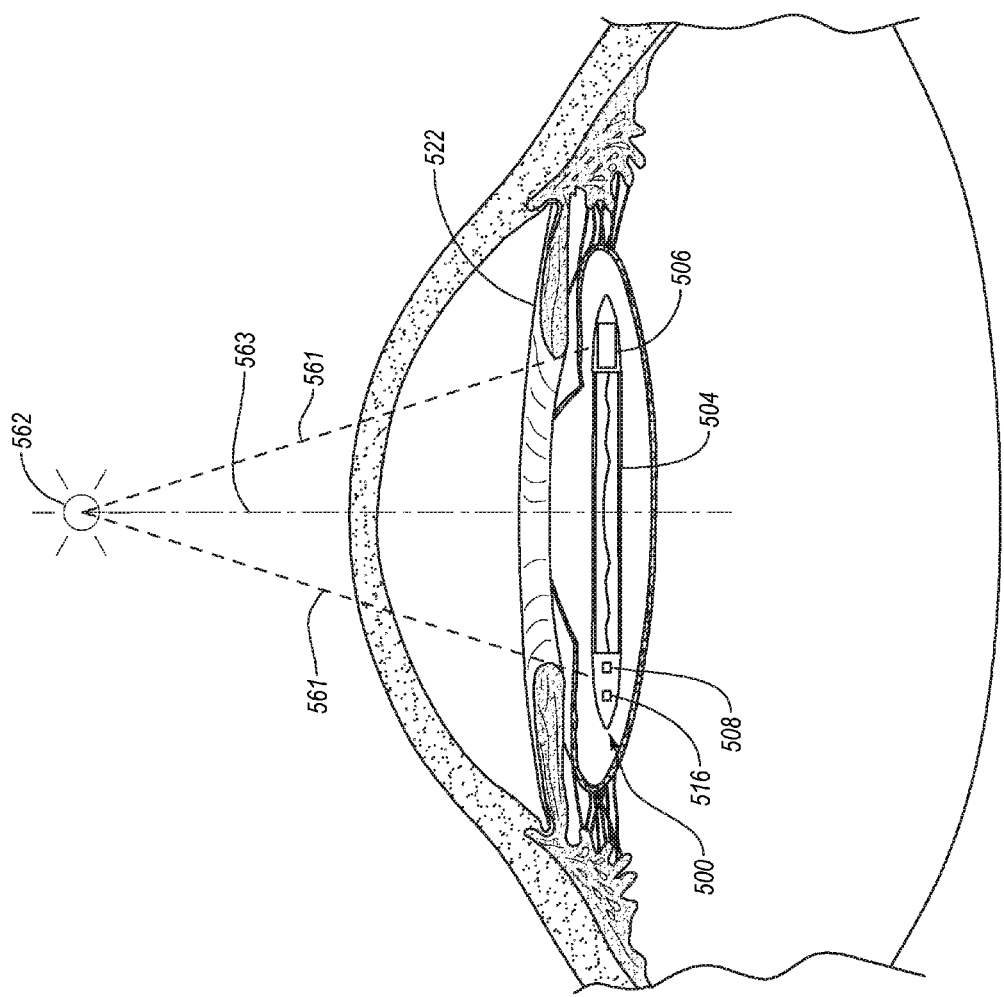
FIGS. 5A and 5B are schematic illustrations of an ophthalmic device including at least one photodetector, according to an embodiment.
Figure 5B:
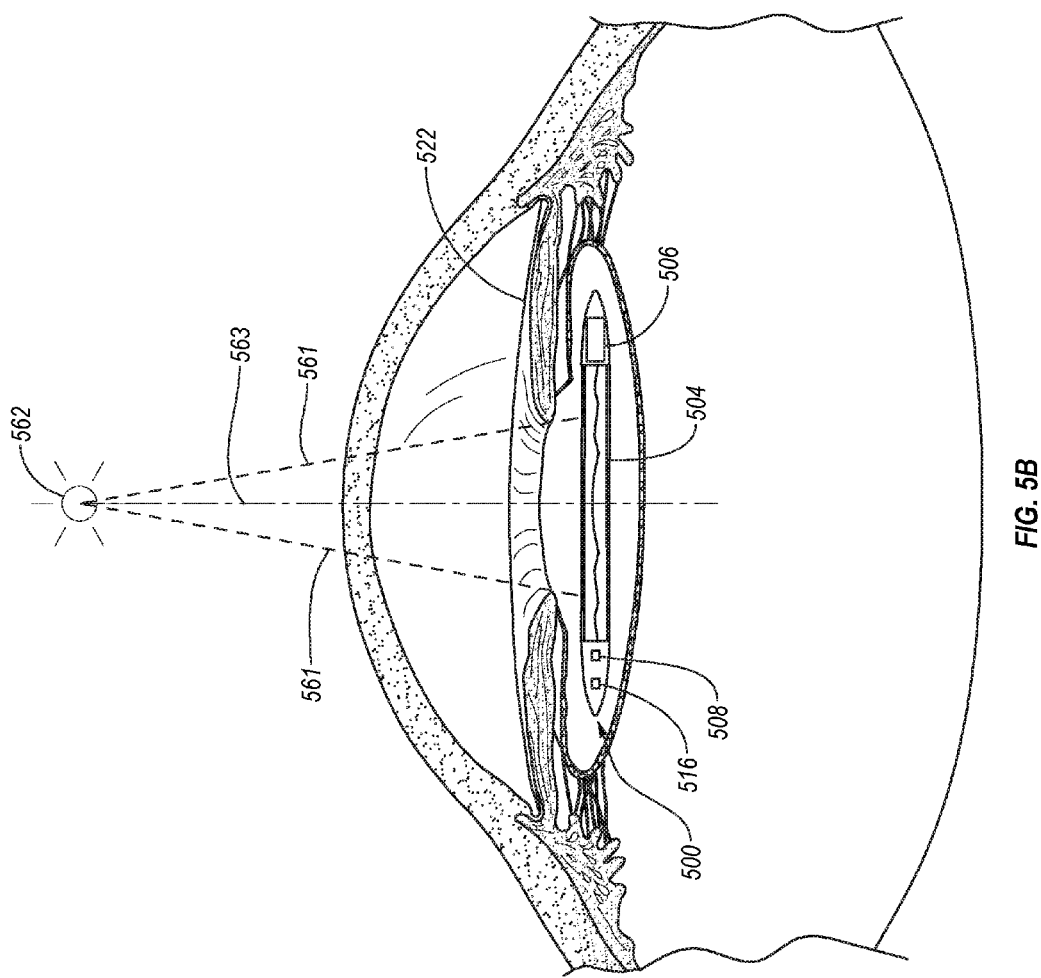

In an embodiment, the second sensor includes at least one photodetector configured to sense one or more electromagnetic signals. FIGS. 5A and 5B are schematic illustrations of an ophthalmic device 500 including at least one photodetector, according to an embodiment. Except as otherwise described herein, the ophthalmic device 500 and its materials, components, or elements can be similar to or the same as the ophthalmic devices 100, 300a-b, 400 (FIGS. 1A-1B and 3-4B) and their respective materials, components, or elements. For example, the ophthalmic device 500 includes at least one switchable lens 504, at least one first sensor 506, and a controller 516. The ophthalmic device 500 or its materials, components, or elements can be used in any of the ophthalmic devices or ophthalmic systems disclosed herein.

The ophthalmic device 500 includes at least one second sensor 508. The second sensor 508 includes at least one photodetector configured to detect one or more electromagnetic signals. In an embodiment, the photodetector can include at least one electro-optical sensor, at least one photoresistor, at least one photovoltaic, at least one photodiode, at least one phototransistor, at least one charge coupled device, at least one infrared detector, fiber optics, at least one transducer, or at least one other suitable sensor.

In an embodiment, the second sensor 508 can include an array. The array includes a plurality of photodetectors. For example, the photodetectors of the array can be positioned in a grid-like pattern, another suitable pattern, or randomly. In an embodiment, the array can be configured such that at least some of the photodetectors are positioned to sense electromagnetic signals from different directions. In an embodiment, the array can be configured such that at least some of the photodetectors are positioned to sense different wavelengths of electromagnetic energy. In an embodiment, the array can be configured to sense when some of the photodetectors are illuminated by the electromagnetic signals or some of the photodetectors are not illuminated by the electromagnetic signals.

Referring to FIG. 5A, the second sensor 508 is at least partially illuminated by at least one electromagnetic signal 561 from an electromagnetic source 562. The electromagnetic source 562 can be a light-emitting diode, an electric discharge light source, an incandescence light source, a luminescence light source, or another suitable light source. In an embodiment, the electromagnetic source 562 is remote from the ophthalmic device 500. In an embodiment, the electromagnetic source 562 is disposed in or on the ophthalmic device 500 and emits the electromagnetic signal 561 from the ophthalmic device 500 that is in turn reflected back toward the second sensor 508. In an embodiment, the electromagnetic source 562 can include a specially made device to emit a selected electromagnetic signal 561 (e.g., an electromagnetic signal exhibiting a selected wavelength, pulsing frequency, or intensity) that the second sensor 508 can sense. In an embodiment, the electromagnetic source 562 can include a man-made electromagnetic source (e.g., a specially made device) or a natural electromagnetic source that emits an electromagnetic signal 561 that the second sensor 508 can sense. In an embodiment, the electromagnetic source 562 can be the source of the electromagnetic signal 561 having high contrast relative to electromagnetic signals thereabout. In an embodiment, the electromagnetic source 562 can be the source of the electromagnetic signal 561 exhibiting sufficient contrast relative to other electromagnetic signals thereabout such that the second sensor 508 can distinguish between the electromagnetic signal 561 generated by the electromagnetic source 562 from the other electromagnetic signals. In an embodiment, the electromagnetic source 562 can include the source(s) of the electromagnetic signals 561 that illuminate at least a portion of the second sensor 508. In an embodiment, the electromagnetic source 562 can be an electromagnetic source currently or at one time was in the optical axis 563, pupillary axis (not shown), line of sight (not shown), visual axis (not shown), or fixation axis (not shown) of the eye 502.

The second sensor 508 can be configured to sense a change in the electromagnetic signals 561 generated by the electromagnetic source 562. In an embodiment, the second sensor 508 can sense an orientation (e.g., change in an orientation) of the electromagnetic source 562 relative to the second sensor 508. The controller 516 can determine vergence rotation when the first sensor 506 senses EMG signals and the second sensor 508 senses a change in the orientation of the electromagnetic source 562. In an embodiment, the second sensor 508 can sense a change in an intensity of the electromagnetic signals 561. The controller 516 can determine there is no vergence rotation when the first sensor 506 senses EMG signals and the second sensor 508 senses a change in the intensity of the electromagnetic signal 561. For example, the controller 516 can determine that the EMG signals sensed by the first sensor 506 are generated by the iris 522 reacting to the change in the intensity of the electromagnetic signal 561. In an embodiment, the second sensor 508 can determine a change in the size of the electromagnetic source 562 or a change in the relative sharpness of an image of the electromagnetic source 562 sensed by the second sensor 508, both of which can determine a proximity of the electromagnetic source 562 relative to the second sensor 508.

Referring to FIG. 5B, in an embodiment, an intensity of the electromagnetic signal 561 that illuminates at least a portion of the second sensor 508 decreases (e.g., ceases to illuminate at least a portion of the second sensor 508). For example, the electromagnetic signal 561 can cease to illuminate the entirety of at least one photodetector, at least one of the photodetectors of an array of photodetectors, or a portion of at least one of the photodetectors. The intensity of the electromagnetic signal 561 can decrease for several reasons, such as contraction of the iris 522, the electromagnetic source 562 decreases the intensity of (e.g., ceases to emit) the electromagnetic signal 561 outputted therefrom, or an orientation of the electromagnetic source 562 relative to the second sensor 508 prevents the electromagnetic signals 561 from illuminating at least a portion of the second sensor 508.

In an embodiment, the controller 516, in conjunction with the first sensing signals from the first sensor 506, can compare the decreased intensity of the electromagnetic signals 561 sensed by the second sensor 508 with the EMG signals sensed by the first sensor 508 to determine whether the focal length of the switchable lens 504 should be selectively switched. For example, the first sensor 506 can sense EMG signals and the second sensor 508 can sense a decreased intensity of the electromagnetic signal 561. In such an example, the controller 516 can determine that contraction of the iris 522 can cause the first sensor 506 to sense EMG signals and the second sensor 508 to sense the decreased intensity of the electromagnetic signals 561. In such a situation, the controller 516 would not direct the switchable lens 504 to alter a focal length thereof.

In an embodiment, the intensity of the electromagnetic signal 561 sensed by the second sensor 508 can increase. The intensity of the electromagnetic signal 561 can increase for several reasons, such as expansion (e.g., dilation) of the iris 522 or the electromagnetic source 562 emits the electromagnetic signal 561. In an embodiment, the controller 516, in conjunction with the first sensing signals from the first sensor 506, can compare the increased intensity of the electromagnetic signals 561 sensed by the second sensor 508 with the EMG signals sensed by the first sensor 508 to determine whether the focal length of the switchable lens 504 should selectively switched. For example, the first sensor 506 can sense EMG signals and the second sensor 508 can sense an increased intensity of the electromagnetic signal 561. In such an example, the controller 516 can determine that expansion of the iris 522 can cause the first sensor 506 to sense EMG signals and the second sensor 508 to sense the increased intensity of the electromagnetic signals 561. In such a situation, the controller 516 would not direct the switchable lens 504 to alter a focal length thereof.

Further examples of ophthalmic devices and ophthalmic systems that include one or more photodetectors configured to sense one or more electromagnetic signals are disclosed in U.S. patent application Ser. No. 14/807,756, filed on Jul. 23, 2015. U.S. patent application Ser. No. 14/807,756 is incorporated herein, in its entirety, by this reference.

Figure 6:
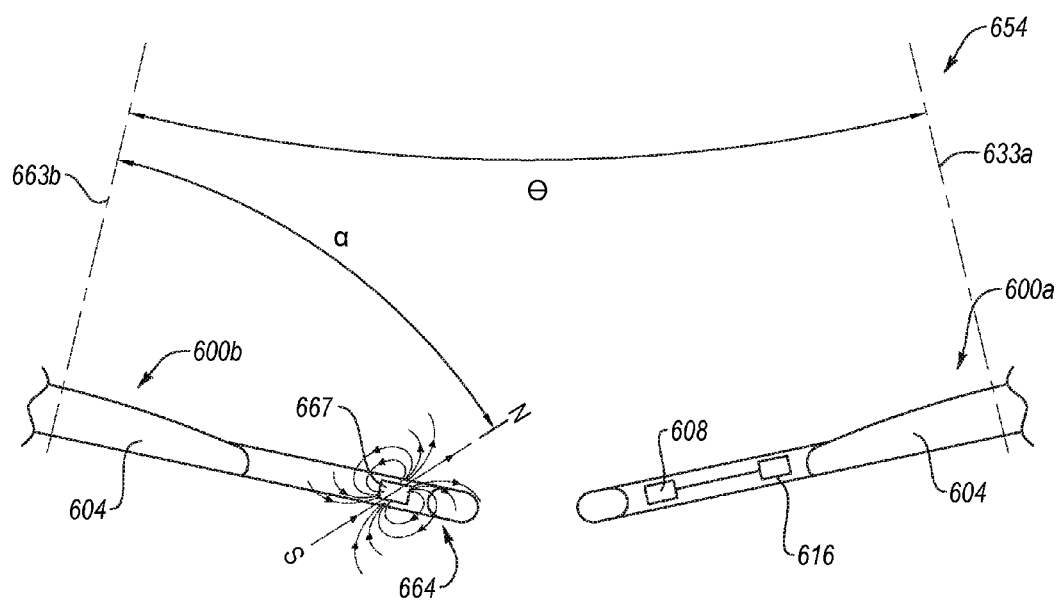
FIG. 6 is a schematic illustration of an ophthalmic system that includes a first ophthalmic device in a first eye and a second ophthalmic device in a second eye, according to an embodiment.

In an embodiment, the second sensor includes a magnetic sensor configured to sense one or more magnetic fields. FIG. 6 is a schematic illustration of an ophthalmic system 654 that includes a first ophthalmic device 600a in a first eye (not shown) and a second ophthalmic device 600b in a second eye (not shown), according to an embodiment. Except as otherwise described herein, the first and second ophthalmic devices 600a, 600b and their materials, components, or elements can be similar to or the same as the ophthalmic devices 100, 300a-b, 400, 500 (FIGS. 1A-1B and 3-5B) and their respective materials, components, or elements. For example, the first and second ophthalmic devices 600a, 600b can each include a switchable lens 604 and at least one first sensor (not shown). The first and second ophthalmic devices 600a, 600b or their materials, components, or elements can be used in any of the ophthalmic devices or ophthalmic systems disclosed herein.

FIG. 6 is a schematic illustration of the first and second ophthalmic devices 600a, 600b with respective first and second optical axes 663a, 663b of the first and second eyes. The first and second optical axes 663a, 663b are oriented to define a first angle θ therebetween, at which the first and second eyes are focused on a first object a first distance from the individual. Focusing the eyes on a second object that is a second distance (different from the first distance) from the individual can cause the first and second optical axis 663a, 663b to be oriented to define a second angle that differs from the first angle θ.

In an embodiment, the first ophthalmic device 600a can include at least one second sensor 608 configured to detect one or more magnetic fields 664. For example, the second sensor 608 can include at least one microelectromechanical magnetic field sensor, at least one Hall effect sensor, at least one magnetoresistance sensor (e.g., ARM magnetometer, GMR magnetometer), at least one induction coil, at least one magnet-diode, at least one magneto-transistor, at least one magnetic tunnel junction magnetometer, at least one magneto-optical sensor, at least one Lorentz force based sensor, at least one electron tunneling based sensor, at least one compass, at least one magnetic transducer, or another suitable magnetic field sensor.

In an embodiment, the second ophthalmic device 600b can include a magnetic field source 667 mounted thereon or embedded therein. The magnetic field source 667 can establish an identifiable magnetic field 664 that can be sensed by the second sensor 608. More specifically, the second sensor 608 can detect a change in an orientation or location of the identifiable magnetic field 664. It should be appreciated that the magnetic field source 667 can be positioned or secured in the individual's second eye without the second ophthalmic device 600b (e.g., the magnetic field source 667 can be implanted in the second eye, such as in the sclera of the second eye). In one or more embodiments, the magnetic field source 667 can move and tilt with the second eye (correspondingly moving the identifiable magnetic field 664), and the second sensor 608 can sense the change in the orientation or location of the identifiable magnetic field 664.

The magnetic field source 667 can include any suitable magnet, which can establish any suitable magnetic field that can vary from one embodiment to the next. In an embodiment, the magnetic field source 667 can be a dipole magnet, a permanent magnet (e.g., a ferromagnet), or a dipole electromagnet. In an embodiment, the magnetic field source 667 can generate a magnetic field 664 having both a dipole and a non-dipole contribution. In such an embodiment, the non-dipole contributions weaken more with distance from the magnetic field source 667 than do the dipole contributions so that at a sufficient distance from the magnetic field source 667 (e.g., at the second sensor 608), the dominant contribution is that of a magnetic dipole. In an embodiment, the electromagnet can be operably coupled to the controller 616 or to an additional controller (e.g., to a controller in the first ophthalmic device 600a), which can turn on or off the electromagnet or can change an intensity of the magnetic field 664 established or generated thereby. For example, the electromagnet can be pulsed to distinguish or identify the magnetic field 664 established thereby from other, interfering magnetic fields that can be present in the individual's environment. Based on the one or more second sensing signals outputted from the second sensor 608, the controller 616 can distinguish the identifiable pulsed magnetic field 664 from other magnetic fields. It should be also appreciated that the second ophthalmic device 600b can include multiple magnets that can establish multiple identifiable magnetic fields.

In an embodiment, the second ophthalmic device 600b can be positioned at a predetermined location or orientation relative to the second optical axis 663b of the second eye. For example, the second ophthalmic device 600b, the identifiable magnetic field 664, or a pole axis (indicated with N and S) of the magnetic field 664 can be oriented relative to the second optical axis 663b of the second eye at a predetermine pitch angle α. The predetermine pitch angle α can be any suitable angle, which can vary from one embodiment to the next. For example, the pitch angle α can be a non-parallel angle (e.g., obtuse or acute angle) relative to the second optical axis 663b. In another example, the pitch angle α can be 0° (i.e., parallel to the second optical axis 663b) or 90° (i.e., perpendicular to the second optical axis 663b).

The second sensor 608 of the first ophthalmic device 600a can be configured to measure the strength and direction of the magnetic field 664, to measure the component of the magnetic field 664 in a specific sensitivity direction, or to include multiple (collocated or not) magnetic sensors each of which is configured to measure separately directed components of the magnetic field 664. In an embodiment, the second sensor 608 includes a sensor configured to measure a magnetic field component oriented at 0° relative to the first optical axis 663a. In an embodiment, the second sensor 608 includes a sensor configured to measure a magnetic field component oriented at 90° relative to the first optical axis 663a (e.g., in the plane of the first ophthalmic device 600a) directed to or away from the second ophthalmic device 600b. The second sensor 608 is positioned in the first ophthalmic device 600a so that as the first eye tilts the sensitivity direction of the second sensor 608 also changes. The value of a specific directional component of magnetic field 664 measured by the second sensor 608 will change based on changes in the tilt of the first eye. It should be further appreciated, that the value of a specific directional component of magnetic field 664 measured by the second sensor 608 will also be changed by changes in the direction the magnetic field source 667, and the accompanying changes in the magnetic field 664 at the location of the second sensor 608. Since the magnetic field source 667 is implanted in the second eye (either directly or indirectly), then field values measured by the second sensor 608 will change based on changes in the tilt of the second eye. Field values measured by the second sensor 608 will change based on changes in the tilt of both the first eye and the second eye.

The controller 616 can be disposed in or on the first or second ophthalmic device 600a, 600b. The controller 616 can be operably coupled to at least one of the switchable lens 604 of the first ophthalmic device 600a or the switchable lens 604 of the second ophthalmic device 600b, in order to switch or direct switch the focal length thereof between different focal lengths.

The first sensor and the second sensor 608 can be configured to transmit one or more first and second sensing signals, respectively, to the controller 616. The controller 616 can compare the first and second sensing signals to determine whether at least one of the switchable lenses 604 should selectively change a focal length thereof. For example, the second sensor 608 can transmit second sensing signals indicating that the second sensor 608 sensed a change in the identifiable magnetic field 664. The controller 616 can compare the sensed change in the magnetic field 664 with the EMG signals sensed by the first sensor to determine whether the change in the magnetic field 664 was caused by vergence rotation or whether the EMG signals were at least partially generated by the ciliary muscle of the first eye. For example, the controller 616 can selectively switch a focal length of the switchable lenses 604 when the first sensor sensed one or more EMG signals and the second sensor 608 senses a change in the magnetic field 664.

Figure 7:
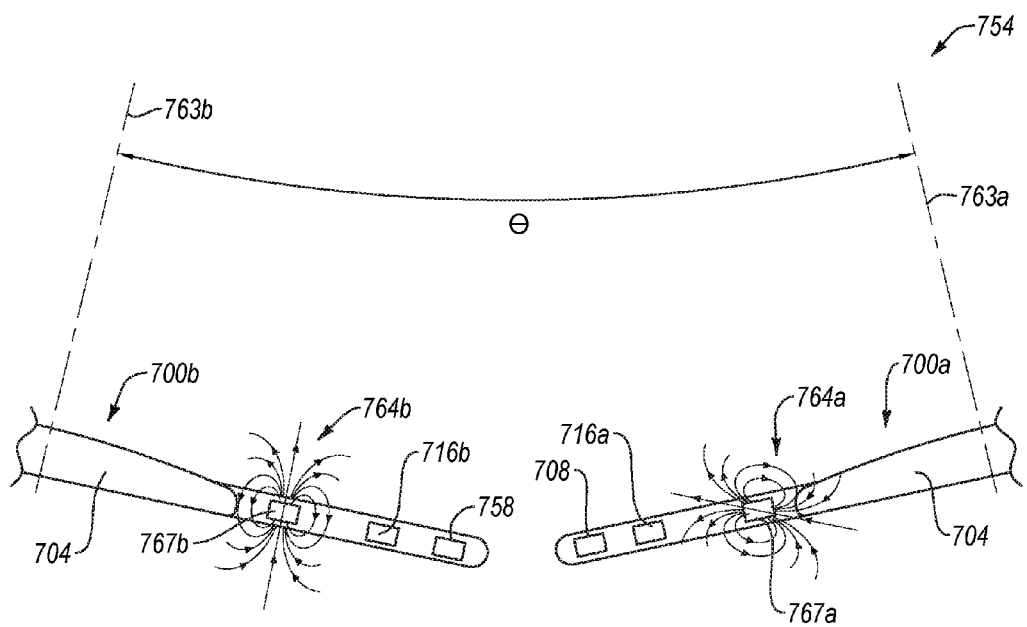
FIG. 7 is a schematic illustration an ophthalmic system that includes a first ophthalmic device in a first eye and a second ophthalmic device in a second eye, according to an embodiment.

The ophthalmic systems disclosed herein can also include multiple identifiable magnetic fields and multiple corresponding magnetic sensors that can detect relative change in a portion or orientation therebetween. FIG. 7 is a schematic illustration of an ophthalmic system 754 that includes a first ophthalmic device 700a in a first eye (not shown) and a second ophthalmic device 700b in a second eye (not shown), according to an embodiment. Except as otherwise described herein, the first and second ophthalmic devices 700a, 700b and their materials, components, or elements can be similar to or the same as the ophthalmic devices 100, 300a-b, 400, 500, 600a-b (FIGS. 1A-1B and 3-6) and their respective materials, components, or elements. For example, the first and second ophthalmic devices 700a, 700b can each include a switchable lens 704. The first and second ophthalmic devices 700a, 700b or their materials, components, or elements can be used in any of the ophthalmic devices or ophthalmic systems disclosed herein.

The first ophthalmic device 700a and the second ophthalmic device 700b at first respective locations or orientations relative to each other when the individual's eyes (not shown) focus or attempt to focus at a first focal length, such that the respective first and second optical axes 763a, 763b of the first and second eye define the first angle θ therebetween. For example, the first ophthalmic device 700a and the second ophthalmic device 700b can be substantially fixed relative to the first and second optical axes 763a, 763b of the individual's eyes.

In an embodiment, the first and second ophthalmic devices 700a, 700a can include at least one first sensor (not shown) and at least one third sensor (not shown), respectively, that that are configured to sense one or more EMG signals (e.g., similar to first and third sensors 306, 356 of FIG. 3). Similarly, the first and second ophthalmic devices 700a, 700b can include at least one second sensor 708 and at least one fourth sensor 758, respectively. The second and fourth sensors 708, 758 can be similar to or the same as the second sensor 608 (FIG. 6) and can sense one or more identifiable magnetic fields (e.g., first identifiable magnetic field 764a or second identifiable magnetic field 764b). In an embodiment, the first and second ophthalmic devices 700a, 700b can also include a first controller 716a or second controller 716b operably coupled to at least one of the first sensor, the second sensor 708, the third sensor, or the fourth sensor 758.

In an embodiment, the first ophthalmic device 700a can include a first magnetic field source 767a that can establish a first identifiable magnetic field 764a and the second ophthalmic device 700b can include a second magnetic field source 767b that can establish a second identifiable magnetic field 764b. The first identifiable magnetic field 764a and second identifiable magnetic field 764b can have any suitable orientation relative to the first optical axis 763a or to the second optical axis 763b of the first eye and second eye. In an embodiment, the first identifiable magnetic field 764a can be oriented at about 90° relative to the first optical axis 763b, and the second identifiable magnetic field 764b can be oriented generally parallel to the second optical axis 763b, or vice versa. The first identifiable magnetic field 764a and second identifiable magnetic field 764b can have any suitable orientation relative to each other. In an embodiment, one of the first or second magnetic field sources 767a, 767b are omitted.

As described above, the second and fourth sensors 708, 758 can sense change in the position or orientation of the respective second identifiable magnetic field 764b and first identifiable magnetic field 764a as the eyes (e.g., the first and second ophthalmic devices 700a, 700b) converge, diverge, or otherwise move. For example, the second sensor 708 can sense a change in the second identifiable magnetic field 764b and can transmit one or more second sensing signals responsive to the sensing. Similarly, the fourth sensor 758 can sense a change in the first identifiable magnetic field 764a and can transmit one or more fourth sensing signals responsive to the sensing. The first or second controllers 716a, 716b can compare the first sensing signals (e.g., from the first sensor), second sensing signals, third sensing signals (e.g., from the third sensor), and fourth sensing signals to determine whether the first or third sensing signals were at least partially generated by the ciliary muscle, the vergence rotation between the eyes, an apparent object distance, etc.

Figure 8:
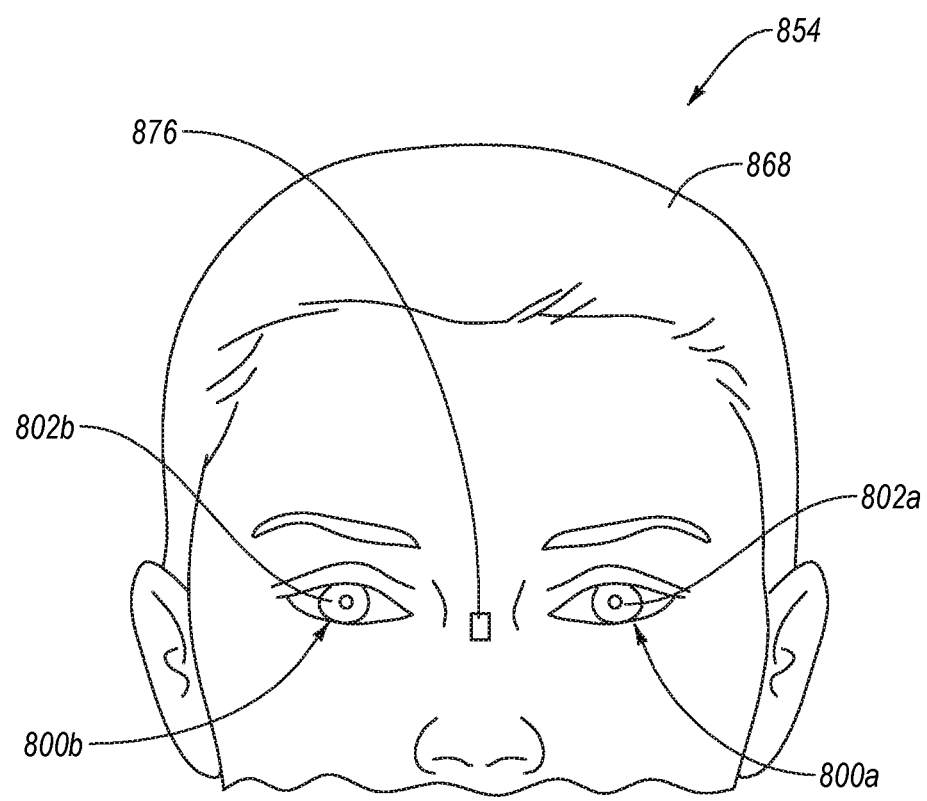
FIG. 8 is a schematic illustration of an ophthalmic system that includes first and second ophthalmic devices and located in the respective first and second eyes of an individual and a magnetic field source positioned externally to the first and second eyes, according to an embodiment.

In an embodiment, an ophthalmic system includes a magnetic field source positioned externally to the individual's eyes. FIG. 8 is a schematic illustration of an ophthalmic system 854 that includes first and second ophthalmic devices 800a and 800b located in the respective first and second eyes 802a, 802b of an individual 868 and a magnetic field source 867 positioned externally to the first and second eyes 802a, 802b, according to an embodiment. Except as otherwise described herein, the first and second ophthalmic devices 800a, 800b and their materials, components, or elements can be similar to or the same as the ophthalmic devices 100, 300a-b, 400, 500, 600a-b, 700a-b (FIGS. 1A-1B and 3-7B) and their respective materials, components, or elements. The ophthalmic system 854 or its materials, components, or elements can be used in any of the ophthalmic devices or ophthalmic systems disclosed herein.

In an embodiment, the magnetic field source 867 can establish an identifiable magnetic field (not shown) that can be detected by one or more sensors in the first or second ophthalmic device 800a, 800b as the individual 868 changes a tilt of the first and second eyes 802a, 802b between a first tilt and the second tilt. The magnetic field source 867 can establish the identifiable magnetic field at any suitable angle relative to the first or second eyes 802a, 802b or to the optical axes thereof (not shown). The magnetic field established by the magnetic field source 867 can remain substantially stationary relative to the individual 868 (e.g., relative to the head of the individual 868). In an embodiment, movement or tilting of the first or second eyes 802a, 802b can produce a corresponding relative movement or tilting between the magnetic field source 867 and the sensors of the ophthalmic system 854 (e.g., the identifiable magnetic field established by the magnetic field source 867 can remain stationary relative to the head of the individual 868, and the sensors of the ophthalmic system 854 can move with the first and second eyes 802a, 802b, such as during vergence rotation).

The magnetic field source 867 can be fixedly positioned relative to the individual 868 with many suitable mechanisms or configurations. For example, the magnetic field source 867 can be implanted near the first eye 802a or second eye 802b of the individual 868 (e.g., near or on the bridge of the nose of the individual 868). Additionally or alternatively, the magnetic field source 867 can be removably positioned on or secured to the individual 868 (e.g., with an adhesive, on a wearable object, such as glasses, etc.). In any embodiment, the magnetic field source 867 can be stationary relative to the head of the individual 868, such that tilting or pivoting of the first and second eyes 802a, 802b can cause relative movement between the first eye 802a and the identifiable magnetic field and between the second eye 802b and identifiable magnetic field.

Further examples of ophthalmic devices and ophthalmic systems that include one or more magnetic sensors and one or more magnetic field sources are disclosed in U.S. patent application Ser. No. 14/807,719, filed on Jul. 23, 2015. U.S. patent application Ser. No. 14/807,719 is incorporated herein, in its entirety, by this reference.

Figure 9:
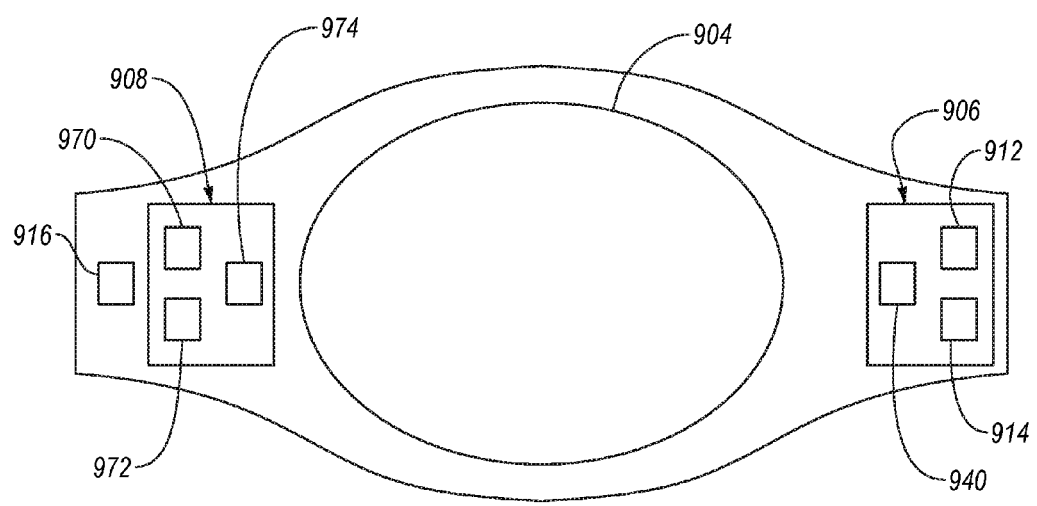
FIG. 9 is a schematic illustration of an ophthalmic device that includes a first sensor and a second sensor each of which is configured to sense one or more EMG signals, according to an embodiment.

FIG. 9 is a schematic illustration of an ophthalmic device 900 that includes first and second sensors 906, 908 each of which is configured to sense one or more EMG signals, according to an embodiment. Except as otherwise described herein, the ophthalmic device 900 and its materials, components, or elements can be similar to or the same as the ophthalmic devices 100, 300a-b, 400, 500, 600a-b, 700a-b, 800a-b (FIGS. 1A-1B and 3-8B) and their respective materials, components, or elements. For example, the ophthalmic device 900 includes a switchable lens 904. The ophthalmic device 900 or its materials, components, or elements can be used in any of the ophthalmic devices disclosed herein.

Similar to the first sensor 106 (FIGS. 1A-1B), the first sensor 906 includes first and second electrodes 912, 914. The first and second electrodes 912, 914 can sense one or more EMG signals. For example, the first and second electrodes 912, 914 can be disposed in or on the ophthalmic device 900 to be at least proximate to a ciliary muscle (not shown) of an eye (not shown). The first sensor 906 can also include a first reference electrode 940.

The second sensor 908 can also be similar or the same first sensor 106 (FIGS. 1A-1B). For example, the second sensor 206 includes third and fourth electrodes 970, 972. The third and fourth electrodes 970, 972 can sense one or more EMG signals at least partially generated by the ciliary muscle or other muscular activity. The second sensor 206 can also include a second reference electrode 974.

In an embodiment, the first and second sensors 906, 908 can transmit one or more first and second sensing signals, respectively, to a controller 916 responsive to sensing one or more EMG signals. The controller 916 can compare the first and second sensing signals to determine whether the switchable lens 904 selectively switches a focal length thereof. In particular, the controller 916 can analyze the differences between the EMG signals sensed by the first and second sensors 906, 908 to determine whether the switchable lens 904 selectively switches a focal length thereof. For example, the controller 916 can determine that a muscle that is closer to the first sensor 906 than the second sensor 908 at least partially generated the EMG signals sensed by the first and second sensors 906,908 when the intensity of the EMG signals sensed by the first sensor 906 are greater than the intensity of the EMG signals sensed by the second sensor 908.

In an embodiment, the second sensor 908 can be disposed in or on a different portion of the ophthalmic device 900 than the first sensor 906. For example, the second sensor 908 can be disposed in or on the ophthalmic device 900 to be more proximate the ciliary muscle or iris of the eye than the first sensor 906. The controller 916 can determine that the ciliary muscle at least partially generated the EMG signals sensed by the first and second sensor 906, 908 when the EMG signals sensed the sensor that is more proximate the ciliary muscle (e.g., one of the first or second sensors 906, 908) exhibits a greater intensity that the EMG signals sensed by the sensor that is more remote from the ciliary muscle (e.g., the other of the first or second sensor 906, 908). The controller 916 can determine that the iris at least partially generated the EMG signals sensed by the first and second sensor 906, 908 when the EMG signals sensed the sensor that is more proximate the iris (e.g., one of the first or second sensors 906, 908) exhibits a greater intensity that the EMG signals sensed by the sensor that is more remote from the iris (e.g., the other of the first or second sensor 906, 908). In another example, the first sensor 906 can be disposed in or on the ophthalmic device 900 to sense EMG signals associated with a first portion of the ciliary muscle and the second sensor 908 can be position in the ophthalmic device 900 to EMG signals associated with a second portion of the ciliary muscle. In such an example, the controller 916 can be able to remove background noise or identify EMG signals associated with the ciliary muscle when the first and second sensors 906, 908 sense EMG signals associated with different portions of the ciliary muscle. In another example, the first sensor 906 can exhibit a first comparative distance and the second sensor 908 can exhibit a second comparative distance. In such an example, the controller 916 can compare the EMG signals sensed by the first and second sensors 906, 908 to determine whether the EMG signals are associated with the ciliary muscle or the iris. In another example, at least one of the first or second electrodes 912, 914 of the first sensor 906 can be disposed in the ophthalmic device 900 and at least one of the third and fourth electrodes 970, 972 of the second sensor 908 can be disposed external the ophthalmic device 900 (e.g., directly contact the ciliary muscle).

Figure 10:
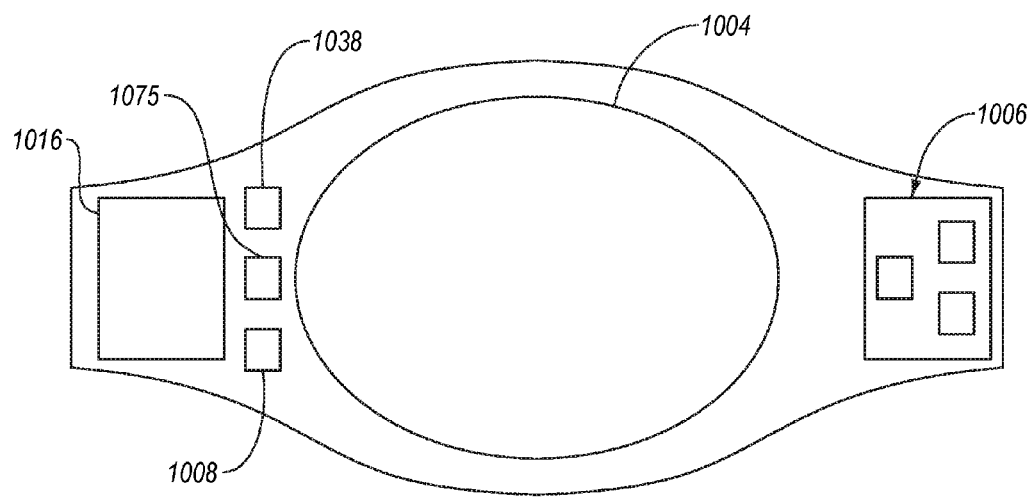
FIG. 10 is a schematic illustration of an ophthalmic device including at least one additional sensor, according to an embodiment.

FIG. 10 is a schematic illustration of an ophthalmic device 1000 including at least one additional sensor 1075, according to an embodiment. Except as otherwise described herein, the ophthalmic device 1000 and its materials, components, or elements can be similar to or the same as the ophthalmic devices 100, 300a-b, 400, 500, 600a-b, 700a-b, 800a-b, 900 (FIGS. 1A-1B and 3-9) and their respective materials, components, or elements. For example, the ophthalmic devices 1000 can include at least one switchable lens 1004, at least one first sensor 1006, at least one second sensor 1008, and a controller 1016. The ophthalmic device 1000 or its materials, components, or elements can be used in any of the ophthalmic devices or systems disclosed herein.

The additional sensor 1075 is disposed in or on the ophthalmic device 1000. The additional sensor 1075 is distinct from the first and second sensors 1006, 1008. In an embodiment, the additional sensor 1075 can be similar to or the same as the first or second sensors 1006, 1008. In an embodiment, the at least one additional sensor 1075 can differ from the first and second sensors 1006, 1008.

In an embodiment, the additional sensor 1075 can sense one or more characteristics that the controller 1016 can use to determine vergence rotation, apparent object distance, etc. For example, the at least one additional sensor 1075 can be substantially similar to the first sensor 1006 and include a plurality of electrodes configured to sense EMG signals. The additional sensor 1075 can be positioned in or on the ophthalmic device 1000 to sense EMG signals generated by a different portion of the ciliary muscle than the first sensor 1006, disposed in or on the ophthalmic device 1000 to be closer or further away from the ciliary muscle than the first sensor 1006, or disposed in or on the ophthalmic device 1000 to be closer or further away from muscular activity not generated by the ciliary muscle (e.g., the iris) than the first sensor 1006. In another example, the at least one additional sensor 1075 can include at least one accelerometer, at least one photodetector (e.g., second sensor 508 of FIGS. 5A-5B), or at least one magnetic field sensor (e.g., second sensor 608, 708 of FIGS. 7-8).

In another embodiment, the additional sensor 1075 can sense one or more characteristics that the controller 1016 does not use to determine vergence rotation, apparent object distance, etc. For example, the additional sensor 1075 can be operably coupled to the switchable lens 1004 and sense the electrical energy stored between the first and second lens electrodes (not shown). For example, the additional sensor 1075 can include a voltmeter (e.g., microelectromechanical system voltmeter) or another suitable electrical sensor. In another example, the additional sensor 1075 can include an electrical sensor that senses power being delivered to one or more components of the ophthalmic device 1000 from the power source 1038. In another example, the additional sensor 1075 can include at least one electrical sensor coupled to the power source 1038 and configure to sense a quantity of electrical power stored therein. In another example, the additional sensor 1075 can sense one or more physiological characteristics of the individual. In an embodiment, the additional sensor 1075 can transmit one or more additional sensing signals responsive to sensing the one or more characteristics.

FIG. 11 is a schematic illustration of an ophthalmic system 1154 that includes an ophthalmic device 1100 and a controller 1116 that is spaced from the ophthalmic device 1100, according to an embodiment. Except as otherwise described herein, the ophthalmic device 1100 and its materials, components, or elements can be similar to or the same as the ophthalmic devices 100, 300a-b, 400, 500, 600a-b, 700a-b, 800a-b, 900, 1000 (FIGS. 1A-1B, 3-10) and their respective materials, components, or elements. For example, the ophthalmic device 1100 includes a switchable lens 1104, a first sensor 1106, and a second sensor 1108. The ophthalmic device 1100 or its materials, components, or elements can be used in any of the ophthalmic systems or ophthalmic devices disclosed herein.

As previously discussed, at least a portion of (e.g., all of) the controller 1116 can be spaced and remote from the ophthalmic device 1100. For example, the controller 1116 can be at least partially disposed in a mobile device, a computer, or another suitable device. The controller 1116 can exhibit increased computing power compared to a controller entirely disposed in the ophthalmic device 1100. For example, the controller 1116 can be larger than a controller entirely disposed in the ophthalmic device 1100 due to the limited size of the ophthalmic device 1100. The increased size of the controller 1116 allows the controller 1116 to include memory storage medium 1148 exhibiting a greater storage capacity or a processor 150 exhibiting processing capabilities greater than a controller that is entirely disposed in the ophthalmic device 1100. However, it is understood that in some embodiments, a portion of the controller 1116 (e.g., the memory storage device 1148 or the processor 1150) can be disposed in the ophthalmic device 1100.

The controller 1116 (e.g., the portions of the controller 1116 spaced from the ophthalmic device 1100) can be operably coupled to the ophthalmic device 1100. For example, the controller 1116 can include a first transceiver 1152 spaced from the ophthalmic device 1100 and the ophthalmic device 1100 can include a second transceiver 1176 that is communicably coupled to the first transceiver 1152. In an embodiment, the first and second sensors 1106, 1108 of the ophthalmic device 1100 can transmit one or more first or second sensing signals, respectively, to the controller 1116 spaced from the ophthalmic device 1100 with the second transceiver 1176. In an embodiment, the controller 1116 can transmit one or more command signals (e.g., responsive to receiving the first and second sensing signals) to the ophthalmic device 1100 with the first transceiver 1152 to the second transceiver 1176. The one or more command signals can include one or more commands to selectively modify the focal length of the at least one switchable lens 1104, one or more commands to sense the EMG signals or characteristics with the first or second sensor 1106, 1108.

Figure 12:
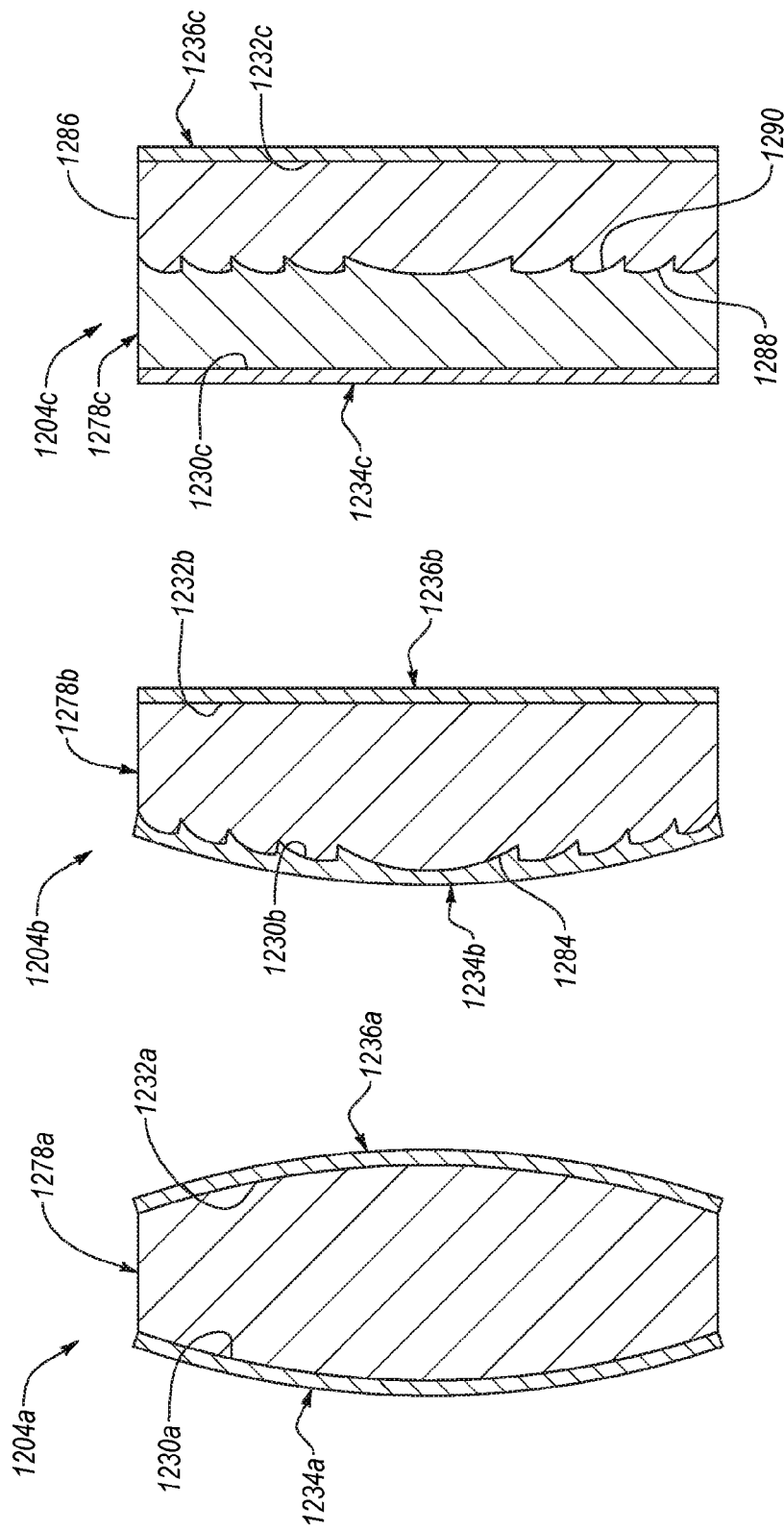
FIGS. 12A-12C are schematic, side cross-sectional views of different switchable lenses, according to an embodiment.

FIGS. 12A-12C are schematic, side cross-sectional views of different switchable lenses, according to an embodiment. Except as otherwise described herein, the switchable lenses 1204a-c and their materials, components, or elements can be similar to or the same as the switchable lenses 104, 304, 404, 504, 604, 704, 804, 904, 1004 (FIGS. 1A-1B, 3-10) and their respective materials, components, or elements. The switchable lenses 1204a-c or their materials, components, or elements can be used in any of the ophthalmic devices disclosed herein.

Referring to FIG. 12A, the switchable lens 1204a can be a variable focus (e.g., switchable) refractive lens. For example, the switchable lens 1204a includes a layer 1278a including at least one electro-optical material. The at least one electro-optical material can include any of the electro-optical materials disclosed herein. The layer 1278a can include a first outer surface 1230a and a second outer surface 1232a opposite the first outer surface 1230a. The switchable lens 1204a can include a first lens electrode 1234a disposed adjacent to (e.g., contact) the first outer surface 1230a and a second lens electrode 1236a disposed adjacent to the second outer surface 1232a. The first and second lens electrodes 1234a, 1236a can selectively apply an electric field to the layer 1278a thereby selectively switching the focal length of the switchable lens 1204a.

Referring to FIG. 12B, the switchable lens 1204b can be a switchable diffractive lens. For example, the switchable lens 1204b can include a layer 1278b including at least one electro-optical material. The at least one electro-optical material can include any of the electro-optical materials disclosed herein. The layer 1278b can include a first outer surface 1230*b* and a second outer surface 1232*b* opposite the first outer surface 1230*b*. The first outer surface 1230*b* can define a diffraction pattern. The switchable lens 1204*b* can include a first lens electrode 1234*b* disposed adjacent to (e.g., contact) the first outer surface 1230*b* and a second lens electrode 1236*b* disposed adjacent to the second outer surface 1232*b*. The first lens electrode 1234*b* can include an inner surface 1284 that corresponds to the diffraction pattern. The first and second lens electrodes 1234*b*, 1236*b* can selectively apply an electric field to the layer 1278*b* thereby selectively switching the focal length of the switchable lens 1204*b*.

Referring to FIG. 12C, the switchable lens 1204*c* can be a switchable diffractive lens including two or more layers. For example, the switchable lens 1204*c* can include a first layer 1278*c* and a second layer 1286. At least one of the first or second layers 1278*c*, 1286 can include at least one electro-optical material. In an embodiment, one of the first or second layers 1278*c*, 1286 can include a passive material (e.g., a substantially electro-optically inert material). The first layer 1278*c* can include a first outer surface 1230*c* and a first diffraction surface 1288 opposite the first outer surface 1230*c*. The first diffraction surface 1288 can define a first diffraction pattern. The second layer 1286 can include a second outer surface 1232*c*. The second outer surface 1232*c* is remote from and generally opposing the first outer surface 1230*c* of the first layer 1278*c*. The second layer 1286 can also include a second diffractive layer 1290 that is opposite the second outer surface 1232*c*. The second diffractive layer 1290 can define a second diffraction pattern that is substantially complementary to the first diffraction pattern of the first diffraction surface 1288. The switchable lens 1204*c* can include a first lens electrode 1234*c* disposed adjacent to (e.g., contact) the first outer surface 1230*c* and a second lens electrode 1236*c* disposed adjacent to the second outer surface 1232*c*. The first and second lens electrodes 1234*c*, 1236*c* can be configured to selectively apply an electric field to the first layer 1278*c* or second layer 1286 thereby selectively switching the focal length of the switchable lens 1204*c*.

Additional examples of switchable lenses are disclosed in U.S. patent application Ser. No. 14/807,673 filed on Jul. 23, 2105, the disclosure of which is incorporated herein, in its entirety, by this reference.

Figure 13:
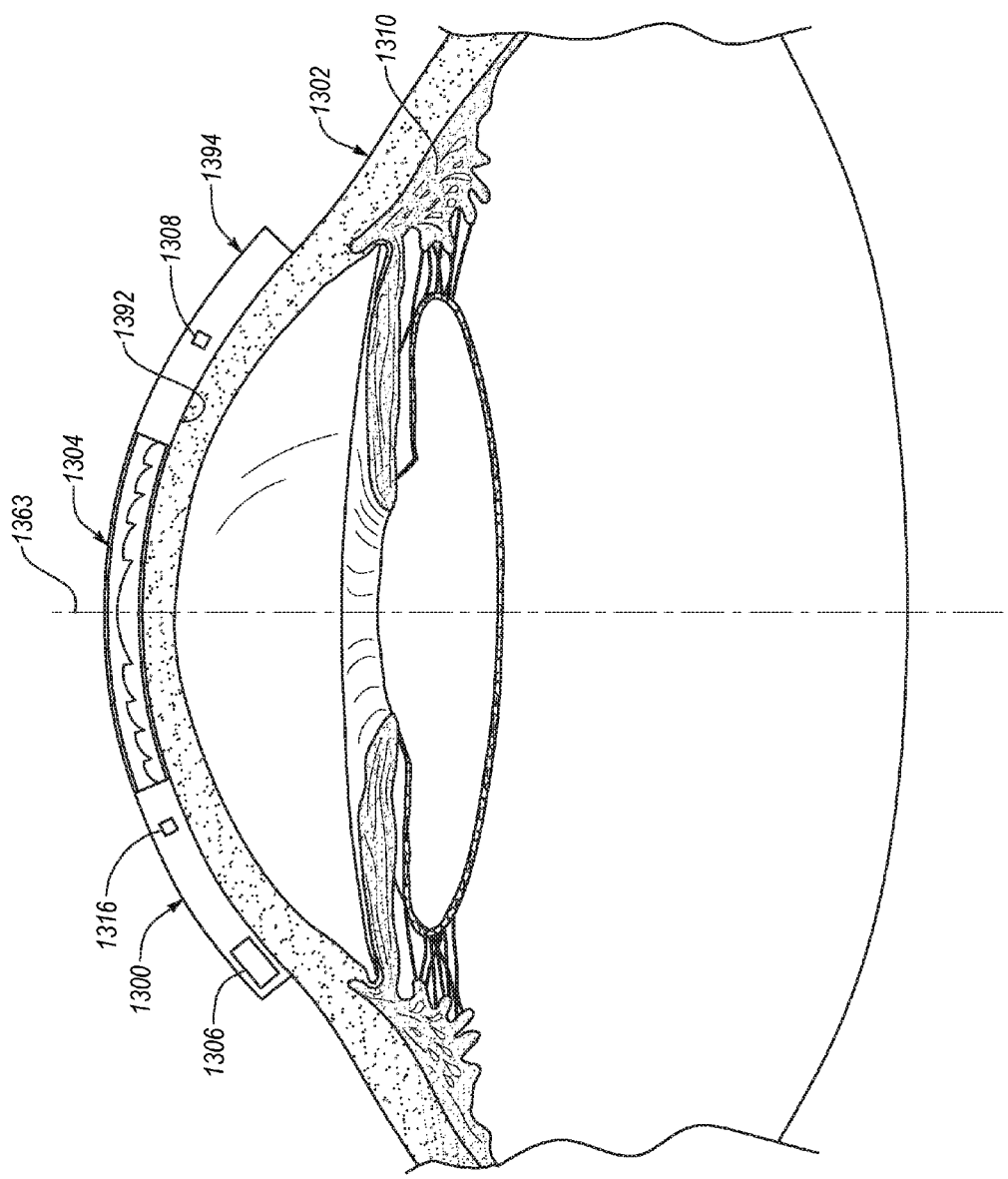
FIG. 13 is a side, cross-sectional view of an ophthalmic device disposed on an outer surface of a cornea of an eye, according to an embodiment.

FIG. 13 is a side, cross-sectional view of an ophthalmic device 1300 disposed on an outer surface of a cornea 1320 of an eye 1302, according to an embodiment. Except as otherwise described herein, the ophthalmic device 1300 and its materials, components, or elements can be similar to or the same as the ophthalmic devices 100, 300*a*-*b*, 400, 500, 600*a*-*b*, 700*a*-*b*, 800*a*-*b*, 900, 1000 (FIGS. 1A-1B and 3-10) and their respective materials, components, or elements. For example, the ophthalmic device 1300 can include a switchable lens 1304, at least one first sensor 1306, at least one second sensor 1308, and a controller 1316. The ophthalmic device 1300 or its materials, components, or elements can be used in any of the ophthalmic devices disclosed herein.

The ophthalmic device 1300 is a contact lens. For example, the ophthalmic device 1300 can include a soft contact lens (e.g., a hydrogel or silicone hydrogel), gas permeable contact lens (e.g., silicone acrylate, fluorosilicone acrylate), a hard contact lens, a hybrid contact lens, or another suitable type of contact lens.

The ophthalmic device 1300 includes an innermost surface 1392 that directly contacts the eye 1302. For example, the innermost surface 1392 can be exhibit a shape that substantially corresponds to the cornea 1320 of the eye 1302. In an embodiment, the ophthalmic device 1300 can be configured to be positioned on the eye 1302 such that the switchable lens 1304 is positioned in at least one of the optical axis 1363, pupillary axis (not shown), line of sight (not shown), visual axis (not shown), or fixation axis (not shown) of the eye 1302. In an embodiment, the ophthalmic device 1300 can be configured to be positioned on the eye 1302 such that the first sensor 1306 senses one or more EMG signals (e.g., EMG signals associated with the ciliary muscle 1310).

In an embodiment, the first sensor 1306, the second sensor 1308, the controller 1316, or another component of the ophthalmic device 1300 can be disposed in or on the switchable lens 1304. For example, the first sensor 1306, the second sensor 1308, the controller 1316, or another component of the ophthalmic device 1300 can be disposed along an outer periphery of the switchable lens 1304. In an embodiment, the ophthalmic device 1300 can include a passive material 1394 coupled to the switchable lens 1304. For example, the passive material 1394 can extend around at least a portion of an outer periphery of the switchable lens 1304. The first sensor 1306, the second sensor 1308, the controller 1316, or another component of the ophthalmic device 1300 can be disposed in the passive material 1394.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In an embodiment, several portions of the subject matter described herein can be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electrical systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context can dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

This disclosure has been made with reference to various example embodiments. However, those skilled in the art will recognize that changes and modifications may be made to the embodiments without departing from the scope of the present disclosure. For example, various operational steps, as well as components for carrying out operational steps, may be implemented in alternate ways depending upon the particular application or in consideration of any number of cost functions associated with the operation of the system; e.g., one or more of the steps may be deleted, modified, or combined with other steps.

Additionally, as will be appreciated by one of ordinary skill in the art, principles of the present disclosure, including components, may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create a means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

In an embodiment, the ophthalmic systems disclosed herein can be integrated in such a manner that the ophthalmic systems operate as a unique system configured specifically for function of changing a focal length of a switchable lens, and any associated computing devices of the ophthalmic systems operate as specific use computers for purposes of the claimed system, and not general use computers. In an embodiment, at least one associated computing device of the ophthalmic systems operates as specific use computers for purposes of the claimed system, and not general use computers. In an embodiment, at least one of the associated computing devices of the ophthalmic systems are hardwired with a specific ROM to instruct the at least one computing device. In an embodiment, one of skill in the art recognizes that the ophthalmic devices and ophthalmic systems effects an improvement at least in the technological field of ophthalmic devices.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A system, comprising:
   at least one ophthalmic device including,
      at least one switchable lens configured to selectively switch a focal length thereof;
      at least one first sensor configured to sense one or more electromyography signals, the at least one first sensor including at least two electrodes, at least one of the at least two electrodes disposed in a portion of the at least one ophthalmic device that is at least proximate to a ciliary muscle of an eye of an individual when the at least one ophthalmic device is placed in or on the eye, the at least one first sensor configured to transmit one or more first sensing signals responsive to sensing one or more electromyography signals; and at least one second sensor that is distinct from the at least one first sensor, the at least one second sensor configured to transmit one or more second sensing signals responsive to sensing one or more characteristics; and at least one controller communicably coupled to the at least one switchable lens, the at least one first sensor, and the at least one second sensor, the at least one controller configured to:

compare the one or more first sensing signals and the one or more second sensing signals to determine that the one or more electromyography signals sensed by the at least one first sensor are generated by at least one of the ciliary muscle or other muscular activity;

when the at least one controller determines that the one or more electromyography signals are generated by the at least one of the ciliary muscle or the other muscular activity, compare the one or more first sensing signals and the one or more second sensing signals to determine a percentage of the one or more electromyography signals sensed by the first sensor that are generated by the ciliary muscle; and direct the at least one switchable lens to selectively switch the focal length thereof responsive to the one or more first sensing signals and the one or more second sensing signals.

2. The system of claim 1, wherein the at least one ophthalmic device includes a first ophthalmic device and a second ophthalmic device.

3. The system of claim 2, wherein each of the first ophthalmic device and the second ophthalmic device includes a transceiver configured to communicably couple the first ophthalmic device and the second ophthalmic device together.

4. The system of claim 2, wherein the at least one controller includes a plurality of controllers, and wherein each of the first ophthalmic device and the second ophthalmic device includes at least one of the plurality of controllers disposed therein or thereon.

5. The system of claim 4, wherein at least one of the plurality of controllers that is disposed in or on the first ophthalmic device is configured to be communicably coupled to at least one of the plurality of controllers that is disposed in or on the second ophthalmic device.

6. The system of claim 1, wherein the at least one switchable lens includes at least one electro-optical material disposed between two substantially transparent electrodes.

7. The system of claim 1, wherein the at least one switchable lens include at least one switchable diffractive lens.

8. The system of claim 7, wherein the at least one switchable diffractive lens includes, a first layer having,
at least one first electro-optical material;
a first outer surface; and
a first diffraction surface defining a first diffraction pattern;

a second layer having,
a second outer surface remote from and generally opposing the first outer surface of the first layer; and
a second diffraction surface defining a second diffraction pattern, wherein, the second diffraction pattern is substantially complementary to the first diffraction pattern;

wherein a first lens electrode is disposed adjacent to the first outer surface of the first layer; and
wherein a second lens electrode is disposed adjacent to the second outer surface of the second layer.

9. The system of claim 8, wherein the second layer includes at least one second electro-optical material.

10. The system of claim 7, wherein the at least one switchable diffractive lens includes, a layer having,
at least one electro-optical material;
a first outer surface; and
a second outer surface defining a first diffraction pattern;

wherein a first lens electrode is disposed adjacent to the first outer surface of the layer; and
wherein a second lens electrode is disposed adjacent to the second outer surface of the layer.

11. The system of claim 1, wherein the at least one switchable lens includes at least one variable focus refractive lens.

12. The system of claim 1, wherein the at least one ophthalmic device includes at least one contact lens.

13. The system of claim 1, wherein the at least one ophthalmic device includes at least one intraocular lens.

14. The system of claim 1, wherein the at least one of the at least two electrodes are configured to directly contact the ciliary muscle when the at least one ophthalmic device is placed in or on the eye.

15. The system of claim 1, wherein the at least one of the at least two electrodes is sized and configured to be disposed in or on a periphery of the at least one ophthalmic device.

16. The system of claim 1, wherein the at least one second sensor is configured to detect one or more characteristics that are different than the one or more electromyography signals.

17. The system of claim 16, wherein the one or more characteristics include at least one acceleration of the eye, at least one electromagnetic signal, at least one magnetic field, or at least one electromyography signal.

18. The system of claim 1, wherein the at least one second sensor includes at least one accelerometer.

19. The system of claim 18, wherein the at least one accelerometer is configured to sense acceleration associated with eye rotation.

20. The system of claim 1, wherein the at least one second sensor includes at least one photodetector.

21. The system of claim 20, wherein the at least one photodetector includes a plurality of photodetectors.

22. The system of claim 20, wherein the at least one photodetector includes a plurality of photodetectors that define a photodetector array.

23. The system of claim 20, wherein the at least one photodetector is configured to sense a change in an intensity of one or more electromagnetic signals sensed by the at least one photodetector, wherein the change in the intensity of the one or more electromagnetic signals is associated with iris contraction or expansion.

24. The system of claim 1, further including,
a magnetic field source sized and configured to be placed in or on a first eye of the individual, the magnetic field source configured to establish an identifiable magnetic field having a predetermined orientation relative to the first eye;

wherein the at least one ophthalmic device includes a first ophthalmic device that is configured to be placed in or on a second eye of the individual; and wherein the at least one second sensor of the first ophthalmic device is configured to detect a change in the established identifiable magnetic field corresponding to a vergence rotation between the first eye and the second eye.

25. The system of claim 24, wherein the at least one ophthalmic device includes a second ophthalmic device configured to be placed in or on the first eye of the individual.

26. The system of claim 25, wherein the second ophthalmic device includes the magnetic field source disposed therein.

27. The system of claim 25, further including, an additional magnetic field source disposed in or on the first ophthalmic device, the additional magnetic field source configured to establish an additional identifiable magnetic field and having a predetermined orientation relative to the second eye;

wherein the at least one second sensor of the second ophthalmic device is configured to detect a change in the additional identifiable magnetic field corresponding to the vergence rotation between the first eye and the second eye.

28. The system of claim 1, further including, a magnetic field source configured to be positioned on the individual, the magnetic field source configured to establish an identifiable magnetic field having a predetermined orientation relative to a first eye of the individual;

wherein the at least one second sensor is configured to detect a change in the identifiable magnetic field corresponding to a vergence rotation between the first eye and a second eye of the individual.

29. The system of claim 1, wherein the at least one second sensor is a different type of sensor than the at least one first sensor.

30. The system of claim 1, wherein the at least one second sensor includes at least two electrodes configured to detect one or more additional electromyography signals.

31. The system of claim 30, wherein the at least two electrodes of the second sensor are disposed in the at least one ophthalmic device to be more remote from the ciliary muscle than the at least two electrodes of the at least one first sensor when the at least one ophthalmic device is placed in or on the eye of the individual.

32. The system of claim 1, further including at least one additional sensor disposed in or on the at least one ophthalmic device, wherein the at least one additional sensor is distinct from the at least one first sensor and the at least one second sensor.

33. The system of claim 32, wherein the at least one additional sensor is different than the at least one first sensor and the at least one second sensor.

34. The system of claim 1, wherein the at least one controller is configured to compare the one or more first sensing signals and the one or more second sensing signals to determine a vergence rotation between a first eye and a second eye of the individual.

35. The system of claim 34, wherein the at least one controller is configured to determine an apparent object distance from the vergence rotation and to direct the at least one switchable lens to selectively switch to a first focal length from a second focal length based on the apparent object distance.

36. The system of claim 1, wherein the at least one controller is configured to compare the one or more first sensing signals and the one or more second sensing signals to determine whether the one or more electromyography signals detected by the at least one first sensor were at least partially generated by the ciliary muscle of the eye.

37. The system of claim 1, wherein at least a portion of the at least one controller is spaced from the at least one ophthalmic device.

38. A system, comprising:

a first ophthalmic device and a second ophthalmic device, each of the first ophthalmic device and the second ophthalmic device including, at least one switchable lens including at least one electro-optical material disposed between two substantially transparent electrodes, the at least one electro-optical material configured to selectively switch a focal length thereof;

at least one first sensor configured to sense one or more electromyography signals, the at least one first sensor including at least two electrodes, at least one of the at least two electrodes disposed in or on a portion of the first ophthalmic device or the second ophthalmic device that is at least proximate to a ciliary muscle of an eye of an individual when the first ophthalmic device or the second ophthalmic device is placed in or on a first eye and a second eye of the individual, respectfully, wherein the at least one first sensor is configured to transmit one or more first sensing signals responsive to sensing the one or more electromyography signals; and at least one second sensor that is distinct from the at least one first sensor, the at least one second sensor configured to transmit one or more second sensing signals responsive to sensing one or more characteristics; and at least one controller communicably coupled to the at least one switchable lens, the at least one first sensor, and the at least one second sensor of the first ophthalmic device and the second ophthalmic device, the at least one controller configured to:

compare the one or more first sensing signals and the one or more second sensing signals of at least one of the first ophthalmic device or the second ophthalmic device to determine a vergence rotation between the first eye and the second eye of the individual; and direct the at least one switchable lens of the first ophthalmic device and the second ophthalmic device to selectively switch the focal length thereof responsive to receiving the one or more first sensing signals and the one or more second sensing signals from the first ophthalmic device and the second ophthalmic device.

39. A method of adjusting a focal length of at least one ophthalmic device, the method comprising:

sensing one or more electromyography signals with at least one first sensor, the at least one first sensor including at least two electrodes, at least one of the at least two electrodes is disposed in a portion of the at least one ophthalmic device that is at least proximate to a ciliary muscle of an eye of an individual that the at least one ophthalmic device is placed in or on;

transmitting one or more first sensing signals from the at least one first sensor to at least one controller responsive to sensing the one or more electromyography signals;

sensing one or more characteristics with at least one second sensor disposed in the at least one ophthalmic device, wherein the at least one second sensor is distinct from the at least one first sensor;

transmitting one or more second sensing signals from the at least one second sensor to the at least one controller responsive to sensing the one or more characteristics;

with the at least one controller that is communicably coupled to the at least one switchable lens, the at least one first sensor, and the at least one second sensor:

comparing the one or more first sensing signals and the one or more second sensing signals to determine that the one or more electromyography signals sensed by the first sensor are generated by at least one of the ciliary muscle or other muscular activity;

when the at least one controller determines that the one or more electromyography signals are generated by the at least one of the ciliary muscle or the other muscular activity, comparing the one or more first sensing signals and the one or more second sensing signals to determine a percentage of the one or more electromyography signals sensed by the at least one first sensor that are generated by the ciliary muscle; and selectively modifying the focal length of at least one switchable lens of the at least one ophthalmic device responsive to the one or more first sensing signals and the one or more second sensing signals.

40. The system of claim 38, wherein the at least one controller is configured to determine an apparent object distance from the vergence rotation and to direct the at least one switchable lens to selectively switch to a first focal length from a second focal length based on the apparent object distance.

* * * * *